US 12,331,087 B2

(12) United States Patent
Lee et al.

(10) Patent No.: US 12,331,087 B2
(45) Date of Patent: Jun. 17, 2025

(54) HUMAN ANTI-ANTXR CHIMERIC ANTIGEN RECEPTOR AND USE THEREOF

(71) Applicant: MJCELL BIO CO., LTD., Gyeonggi-do (KR)

(72) Inventors: Kyung-Mi Lee, Seoul (KR); Seung-Hyun Jeon, Seoul (KR); Baeckseung Lee, Seoul (KR); Yoon Lee, Gyeonggi-do (KR); Young-Kwan Lee, Seoul (KR)

(73) Assignee: MJCELL BIO CO., LTD., Gyeonggi-Do (KR)

( * ) Notice: Subject to any disclaimer, the term of this patent is extended or adjusted under 35 U.S.C. 154(b) by 973 days.

(21) Appl. No.: 17/311,619

(22) PCT Filed: Dec. 6, 2019

(86) PCT No.: PCT/KR2019/017215
§ 371 (c)(1),
(2) Date: Jun. 7, 2021

(87) PCT Pub. No.: WO2020/117004
PCT Pub. Date: Jun. 11, 2020

(65) Prior Publication Data
US 2022/0372084 A1   Nov. 24, 2022

(51) Int. Cl.
*C07K 14/32* (2006.01)
*A61K 40/11* (2025.01)
*A61K 40/31* (2025.01)
*A61K 40/42* (2025.01)
*A61P 1/18* (2006.01)
*A61P 35/00* (2006.01)
*C07K 14/705* (2006.01)
*C07K 14/725* (2006.01)

(52) U.S. Cl.
CPC .............. *C07K 14/32* (2013.01); *A61K 40/11* (2025.01); *A61K 40/31* (2025.01); *A61K 40/4202* (2025.01); *A61K 40/4269* (2025.01); *A61P 1/18* (2018.01); *A61P 35/00* (2018.01); *C07K 14/7051* (2013.01); *C07K 14/70517* (2013.01); *C07K 14/70521* (2013.01); *C07K 14/70578* (2013.01); *A61K 2239/31* (2023.05); *A61K 2239/38* (2023.05); *A61K 2239/54* (2023.05); *C07K 2319/02* (2013.01); *C07K 2319/03* (2013.01); *C07K 2319/33* (2013.01)

(58) Field of Classification Search
CPC .............. C07K 14/32; C07K 14/7051; C07K 14/70517; C07K 14/70521; C07K 14/70578; C07K 2319/02; C07K 2319/03; C07K 2319/33; C07K 16/28; C07K 14/705; A61K 35/17; A61K 39/4631; A61K 39/464402; A61K 39/464488; A61K 48/00; A61P 1/18; A61P 35/00; C12N 2740/16043
See application file for complete search history.

(56) References Cited

U.S. PATENT DOCUMENTS

| | | | |
|---|---|---|---|
| 9,346,860 B2 * | 5/2016 | Williamson | ............ A61P 31/04 |
| 2013/0280220 A1 | 10/2013 | Ahmed et al. | |
| 2016/0015750 A1 * | 1/2016 | Gottschalk | ......... C07K 16/2851 |
| | | | 435/325 |
| 2016/0264662 A1 | 9/2016 | Dimitrov et al. | |
| 2017/0096638 A1 | 4/2017 | Wu | |
| 2017/0114133 A1 | 4/2017 | Saha et al. | |

FOREIGN PATENT DOCUMENTS

| | | |
|---|---|---|
| CN | 108707199 A | 10/2018 |
| JP | 2018530315 A | 10/2018 |
| WO | 2008063147 A2 | 5/2008 |
| WO | 2017035508 A1 | 3/2017 |
| WO | 2018075820 A2 | 4/2018 |

OTHER PUBLICATIONS

Bradley, KA et. al. "Identification of the cellular receptor for anthrax toxin", 2001, Nature, 414, 225-229. (Year: 2001).*
Office Action Issued in Chinese Patent Application No. 201980091396.6 on Jul. 17, 2023.
Search Report Issued in Chinese Patent Application No. CN201980091396.6 on Jul. 5, 2023.
Office Action issued on Apr. 3, 2024 for Chinese Patent Application 201980091396.6.
English Translation of Office Action issued on Apr. 3, 2024 for Chinese Patent Application 201980091396.6.
Search Report issued on Apr. 2, 2024 for Chinese Patent Application 201980091396.6.

(Continued)

*Primary Examiner* — Nelson B Moseley, II
*Assistant Examiner* — Alyssa Rae Stonebraker
(74) *Attorney, Agent, or Firm* — HULTQUIST, PLLC; Steven J. Hultquist

(57) ABSTRACT

The present invention relates to a chimeric antigen receptor having a ligand specifically targeting an anthrax toxin receptor (ANTXR), and, more specifically, to: a nucleic acid encoding a chimeric antigen receptor comprising ligand PA63 specifically binding to anthrax toxin receptor 1 (ANTXR1) or anthrax toxin receptor 2 (ANTXR2); a vector comprising the nucleic acid encoding a chimeric antigen receptor; and a recombinant cell comprising the vector; a pharmaceutical composition for preventing or treating solid cancer, comprising the recombinant cell; and a treatment method. Solid cancer can be treated using an anti-ANTXR chimeric antigen receptor (CAR)-T cell, according to the present invention, and since the chimeric antigen receptor (CAR)-T cell is administered to patients with solid cancer for whom anti-cancer drug administration is not effective, especially patients with pancreatic cancer, drug administration is limited, and customized solid cancer prevention or treatment, which are efficient and safe, is possible.

16 Claims, 9 Drawing Sheets
Specification includes a Sequence Listing.

(56) References Cited

OTHER PUBLICATIONS

Mamillapalli, S., et al., "Stability of domain 4 of the anthrax toxin protective antigen and the effect of the VWA domain of CMG2 on stability", Protein Science, 2016, DOI 10.1002/pro.3087, Publisher: The Protein Society.

Byrd, T.T., et al., "TEM8/ANTXR1-specific CAR T cells as targeted therapy for triple-negative breast cancer", cancerres.aacrjournals. org, 2017, pp. DOI:10.1158/0008-5472.CAN-16-1911, Publisher: American Association for Cancer Research.

Carson-Walter et al., 2001 "Cell Surface Tumor Endothelial Markers Are Conserved in Mice and Humans," Cancer Res 61:6649-55.

Hruban et al., 2001 "Pancreatic Intraepithelial Neoplasia, A New Nomenclature and Classification System for Pancreatic Duct Lesions," Am J Surg Pathol 25(5):579-86.

Liu et al., 2014 "Anthrax lethal and edema toxins in anthrax pathogenesis," Trends Microbiol 22(6):317-25.

Nanda and St. Croix, 2004 "Tumor endothelial markers: new targets for cancer therapy," Curr Opin Oncol 16:44-49.

NCBI, GenBank accession No. 3INO_A (2017.11.14) (2 pages).

NCBI, GenBank accession No. AAM26109.1 (2016.07.26) (2 pages).

Ottenhof et al., 2009 "Pancreatic Intraepithelial Neoplasia and Pancreatic Tumorigenesis, Of Mice and Men," Arch Pathol Lab Med 133:375-81.

Sipos et al., 2009 "Pancreatic Intraepithelial Neoplasia Revisited and Updated," Pancreatology 9:45-54.

St. Croix et al., 2000 "Genes Expressed in Human Tumor Endothelium," Science 289:1197-1202.

Williams et al., 2009 "Domain 4 of the anthrax protective antigen maintains structure and binding to the host receptor CMG2 at low pH," Protein Sci 18:2277-86.

Ye et al., 2014 "Therapeutic potential of capillary morphogenesis gene 2 extracellular vWA domain in tumour-related angiogenesis," Int J Oncol 45(4):1565-73.

International Search Report for related Application No. PCT/KR2019/017215, mailed Apr. 6, 2020 (4 pages).

Written Opinion for related Application No. PCT/KR2019/017215, mailed Apr. 6, 2020 (4 pages).

* cited by examiner

HUMAN ANTI-ANTXR CHIMERIC ANTIGEN RECEPTOR AND USE THEREOF

REFERENCE TO SEQUENCE LISTING SUBMITTED VIA EFS-WEB

The instant application contains a Sequence Listing which has been submitted electronically in ASCII format and is hereby incorporated by reference in its entirety as a part of the present specification and application. Such ASCII format Sequence Listing, entitled 595_SeqListing_ST25.txt, was created on Dec. 10, 2021, and is 35,342 bytes in size.

1. TECHNICAL FIELD

The present invention relates to a chimeric antigen receptor comprising a ligand specifically targeting an anthrax toxin receptor (ANTXR), and more specifically to a nucleic acid encoding a chimeric antigen receptor comprising a PA63 ligand specifically binding to an anthrax toxin receptor 1 (ANTXR1) or an anthrax toxin receptor 2 (ANTXR2), a vector comprising the nucleic acid encoding the chimeric antigen receptor, a recombinant cell comprising the vector, a pharmaceutical composition for preventing or treating solid cancer comprising the recombinant cell, and a method of treating solid cancer using the same.

1. BACKGROUND ART

An anthrax toxin receptor (ANTXR) includes anthrax toxin receptor 1 (ANTXR1) and anthrax toxin receptor 2 (ANTXR2), and its known ligands include anthrax toxins secreted by anthrax bacteria. Anthrax toxins are secreted by *Bacillus anthracis*, which is a gram-positive bacterium, and comprise three toxin proteins, namely protective antigen (PA, 83 kDa), lethal factor (LF, 90 kDa) and edema factor (EF, 89 kDa) (Morton, N. (2001) New Engl. J. Med. 345:1621-1626). Among these, PA binds to the anthrax toxin receptor (ANTXR) on the cell surface, and a 63 kDa protein (PA63), in which the amino terminal 20 kDa (PA20) is cleaved by a furin protease, forms a heptamer, which is then bound with LF (Collier, R. J. (2003) Annu. Rev. Cell Dev. Biol. 19: 45-70).

ANTXR1 is an extracellular matrix protein, and is also called "TEM8 (tumor endothelial marker 8)". ANTXR1, which is a type I transmembrane protein expressed in the endothelium of various tumors, has already been found to be actively expressed during tumor angiogenesis (St. Croix et al., (2000) Sciences 289:1197), and is also known to be involved in the adhesion and migration of cells via extracellular matrix proteins in vascular endothelial cells of tumors (Bradely et al., (2001) Nature 414:228-229; Nanda et al., (2004) Curr. Opin. Oncol. 16:44-49). Because ANTXR1 acts as a receptor for extracellular ligands, it has been a target for the treatment of angiogenesis (Carson-Walter, E B et al., (2001) Cancer Res 61:6649). However, the effects of ANTXR1 on pancreatic cancer tissue have not yet been reported. ANTXR2 is also called "CMG2 (capillary morphogenesis gene 2)", and is known to be involved in angiogenesis. In addition, ANTXR2 is known to be involved in adhesion and motility of several types of cells, including epithelial cells and endothelial cells (Lin Ye et al., (2014) INTERNATIONAL JOURNAL OF ONCOLOGY 45: 1565-1573).

Although advances have been made in the detection, prevention, and treatment of cancer, generally successful treatment strategies have not yet been realized. Various forms of adverse events to cancer treatments result from conventional methods of treating cancer, including chemotherapy and radiotherapy. Therefore, these methods are of limited usefulness due to severe toxicity-associated side effects Immunotherapy using therapeutic antibodies has resulted in limited success due to poor pharmacokinetic profiles, rapid removal of antibodies by serum proteases, filtration in the glomerulus, limited penetration into tumor sites, and the level of expression of target antigens on tumor cells.

In recent years, therapy using genetically modified cells has attracted great attention as a novel quantum immunological gene therapy for cancer. This therapy includes introducing a nucleic acid encoding a chimeric antigen receptor (CAR) having specificity to a cancer cell surface antigen and the ability to activate cells into T cells or NK cells, proliferating the obtained transgenic cells in vitro, and injecting the same. Compared to antibody drugs, this therapy is considered to have a more potent anticancer effect for a longer period of time and is thus expected to be clinically effective.

Against this technical background, as a result of extensive efforts to develop a novel chimeric antigen receptor for treating solid cancer, the present inventors found that ANTXR1 and ANTXR2 are expressed very little in normal tissues, but are specifically expressed only in pancreatic cancer tissues, and found PA63 ligands specifically targeting ANTXR1 and ANTXR2. The present invention was completed based on this finding.

The information disclosed in the Background Art is provided only for better understanding of the background of the present invention, and therefore it may not include information that forms the prior art that is already obvious to those skilled in the art.

2. SUMMARY OF THE INVENTION

It is one object of the present invention to provide a nucleic acid encoding a chimeric antigen receptor (CAR) comprising an extracellular binding domain, a transmembrane domain, and an intracellular signaling domain, wherein the extracellular binding domain recognizes an anthrax toxin receptor (ANTXR).

It is another object of the present invention to provide a vector comprising the nucleic acid encoding the chimeric antigen receptor, a recombinant cell comprising the vector, a pharmaceutical composition for preventing or treating solid cancer comprising the recombinant cell, and a method of treating solid cancer using the same.

To achieve the above objects, the present invention provides a nucleic acid encoding a chimeric antigen receptor (CAR) comprising an extracellular binding domain, a transmembrane domain, and an intracellular signaling domain, wherein the extracellular binding domain recognizes an anthrax toxin receptor (ANTXR).

The present invention also provides a vector comprising the nucleic acid encoding the chimeric antigen receptor (CAR).

The present invention also provides a recombinant cell comprising the vector.

The present invention also provides a pharmaceutical composition for preventing or treating solid cancer comprising the recombinant cell.

The present invention also provides a method of preventing or treating solid cancer comprising administering the recombinant cell to a subject.

The present invention also provides the use of the recombinant cell for the prevention or treatment of solid cancer.

The present invention also provides the use of the recombinant cell for the preparation of a therapeutic agent for preventing or treating solid cancer.

3. BRIEF DESCRIPTION OF THE DRAWINGS

FIG. 1 shows the protein expression levels of six primarily selected genes in normal tissues. A shows the protein expression level of ANTXR1 (anthrax toxin receptor 1), B shows the protein expression level of ANTXR2 (anthrax toxin receptor 2), C shows the protein expression level of TMC5 (transmembrane channel-like 5), D shows the protein expression level of CLDN18 (claudin-18), E shows the protein expression level of MUC13 (mucin 13), and F shows the protein expression level of MMP14 (matrix metallopeptidase 14).

FIG. 2 shows the expression levels of ANTXR1 and ANTXR2 mRNA analyzed through real-time RT-PCR (RT-PCR) in peripheral blood mononuclear cells (PBMCs) and primary pancreatic cancer tissues. PBMC was used as a negative control, PANC-1 was used as a positive control, #101, #103, #105, #106, #107, #108, #109 and #110 were used as stage-2 pancreatic cancer tissues, and #102 was used as a stage-3 pancreatic cancer tissue.

Figure 5:
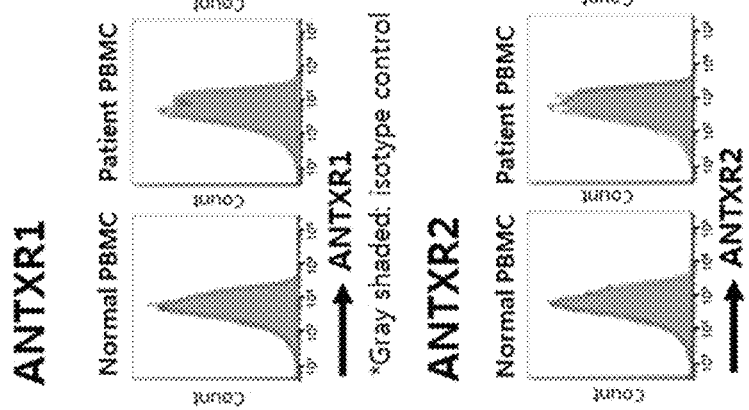

FIG. 5 shows expression levels of cell surface proteins, ANTXR1 and ANTXR2, analyzed by flow cytometry, after treatment with a reagent conjugated with FITC exhibiting fluorescence in PA63 which is a ligand of ANTXR1 and ANTXR2 in HUVEC cells (normal cells), MDA-MB 231 cells, and pancreatic cancer cell lines (AsPC1, Capan2, PANC1, Mia-PaCa2, SNU-213, SNU-324, SNU-2466, SNU-2469, SNU-2485 and SNU-2543) found to have remarkably increased expression of ANTXR1 and ANTXR2 mRNA.

Figure 6:
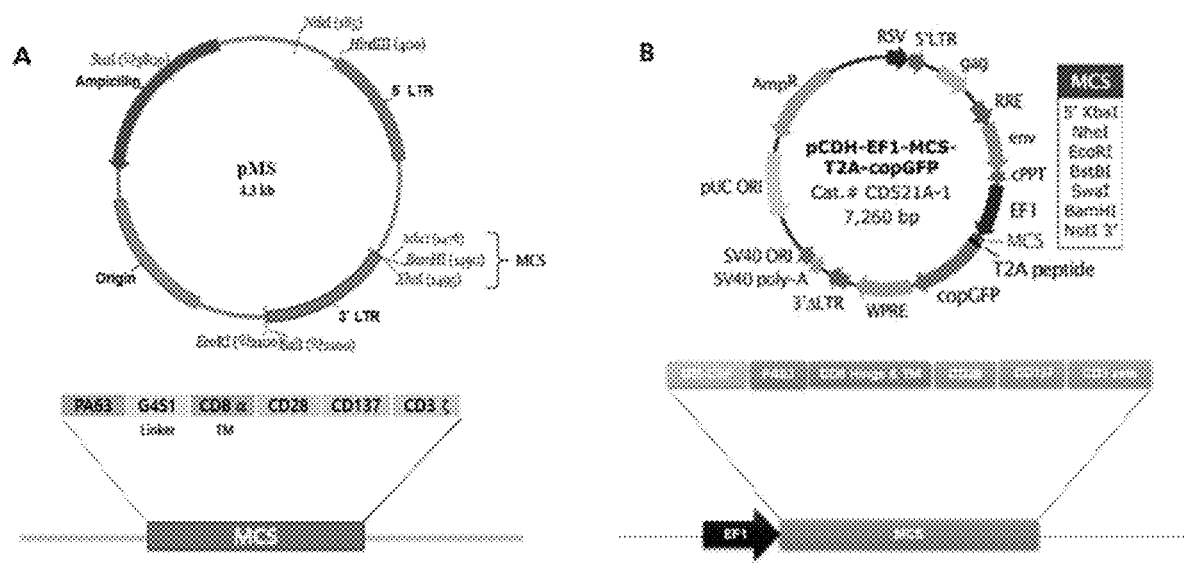

FIG. 6A is a vector map showing the design of a CAR specific to ANTXR1 or ANTXR2 comprising a PA63 ligand as an extracellular binding domain, a transmembrane domain derived from CD8a, a G4S1 (GGGGS) linker, a CD3ζ chain as a primary signaling domain, and CD28 and CD137 as co-stimulatory signaling domains.

FIG. 6B is a vector map showing the design of a CAR specific to ANTXR1 or ANTXR2 comprising domain 4 indispensable for binding of the PA63 ligand to the receptor or a fragment comprising the domain 4, as an extracellular binding domain, a hinge region and transmembrane domain derived from CD8a, a CD32 chain as a primary signaling domain, and CD28 and CD137 as co-stimulatory signaling domains.

Figure 7:
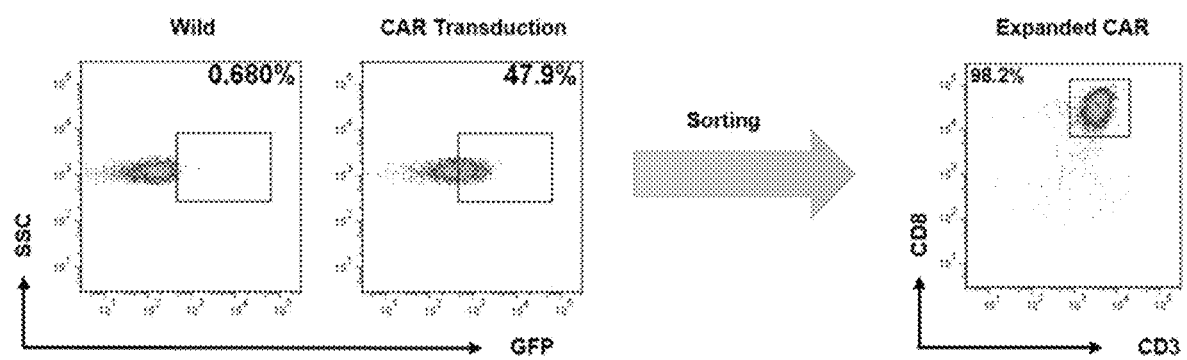

FIG. 7 shows expression resulting from transduction of the CAR into cytotoxic T-cell clones, analyzed through flow cytometry.

Figure 8:
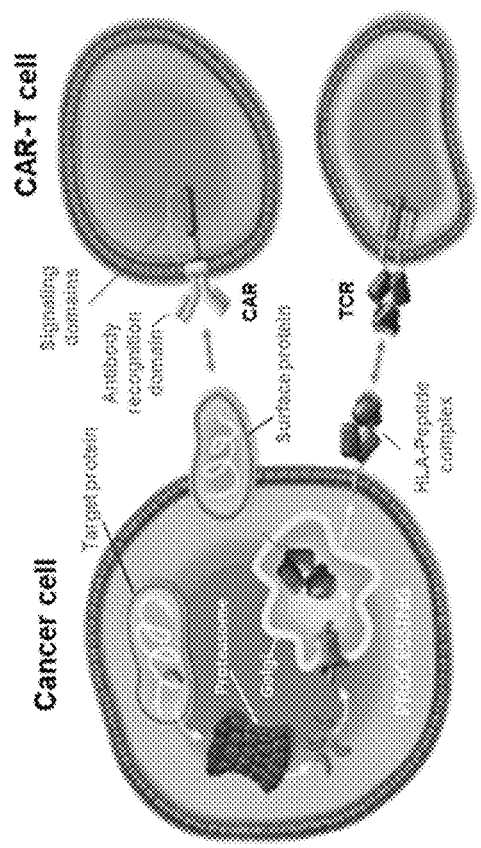

FIG. 8 shows conventional NYESO-1 CTL, which recognizes an NYESO-1 antigen and exhibits activity, and CAR-T cells, which are capable of simultaneously targeting NYESO-1 and ANTXR1 or ANTXR2 by introducing a CAR thereto.

Figure 9:
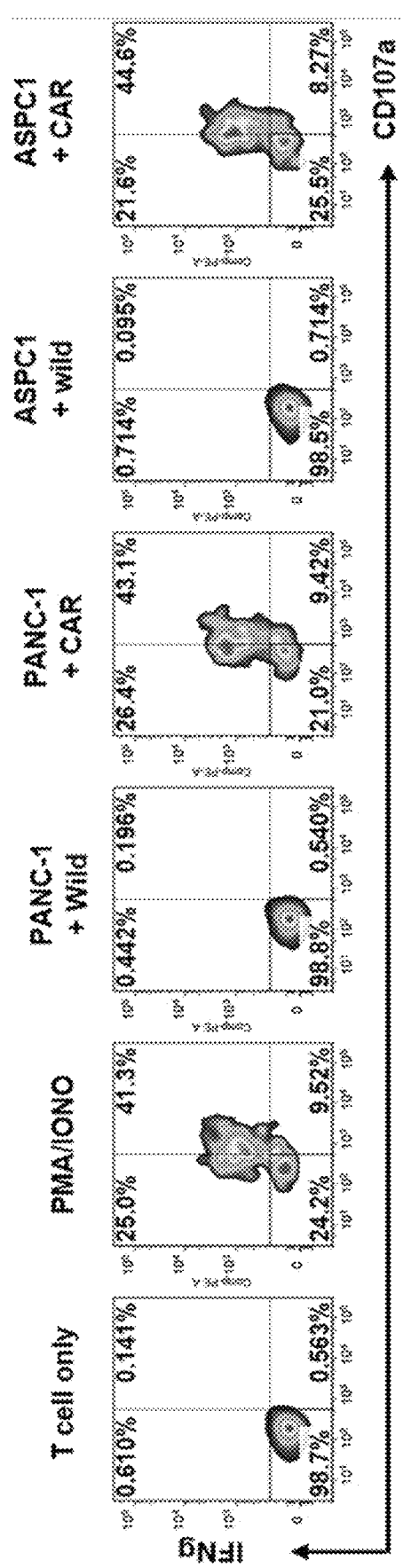

FIG. 9 shows the anticancer cytotoxicity and activity of CAR-T cells comprising D4 against pancreatic cancer cell lines (PANC-1, AsPC1), analyzed using flow cytometry, wherein "T cell only" indicates a negative control and "PMA/Ionomycin" indicates a positive control.

Figure 10:
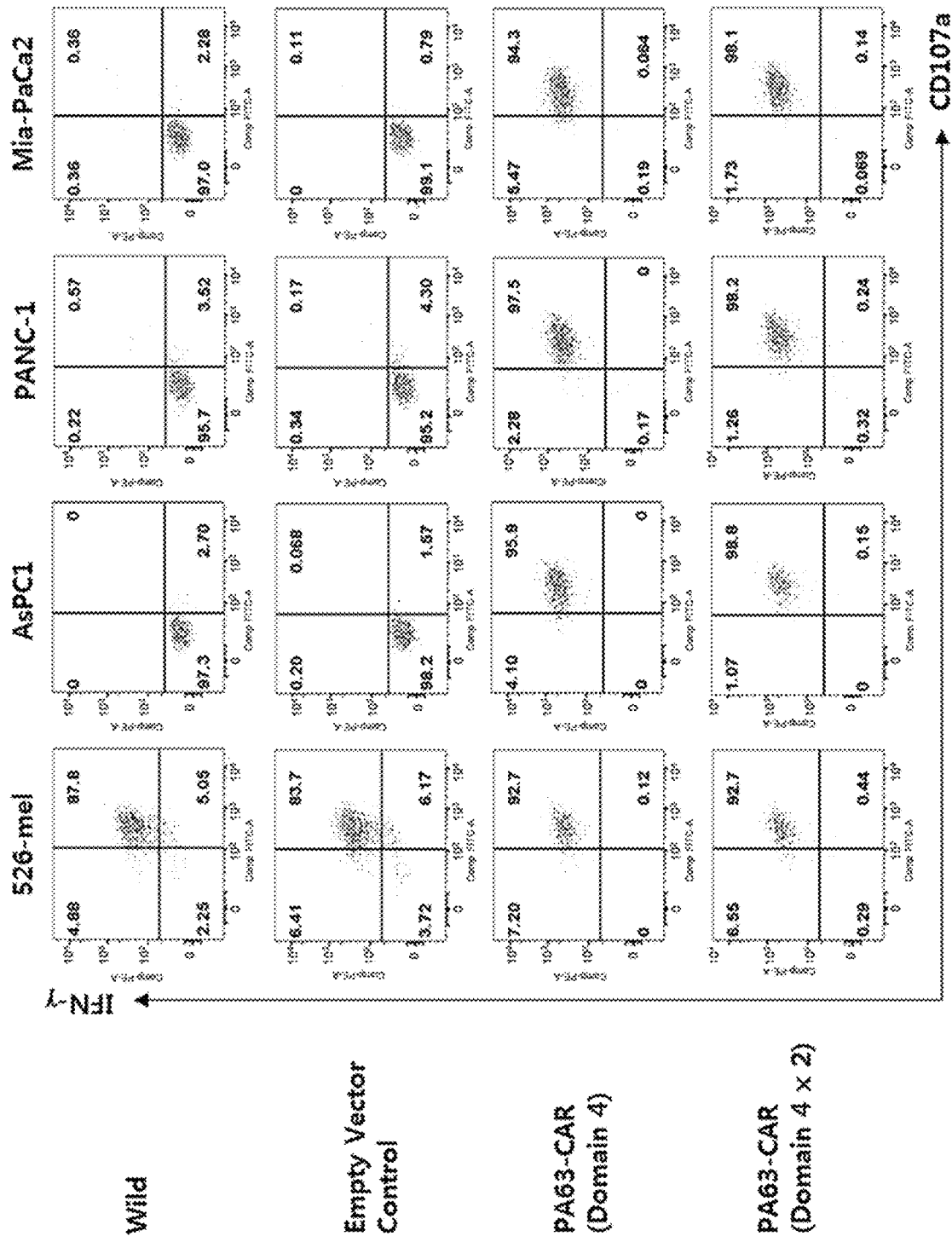

FIG. 10 shows the anticancer cytotoxicity and activity of CAR-T cells comprising D4 or D4+D4 against pancreatic cancer cell lines (AsPC1, PANC-1, Mia-PaCa2).

Figure 11:
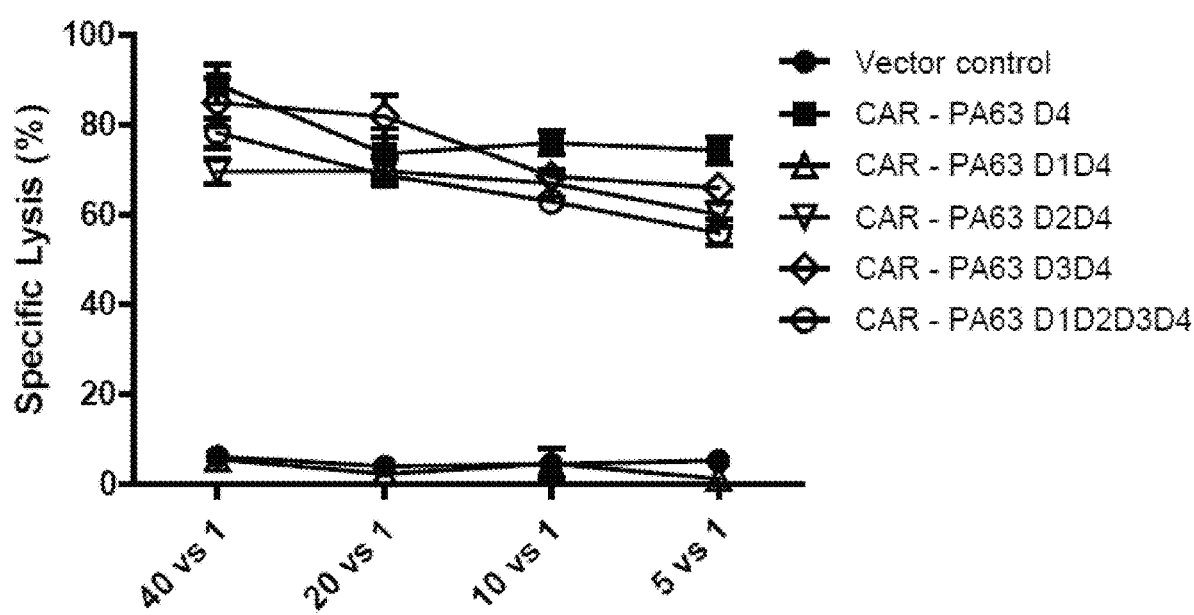

FIG. 11 is a graph showing the anticancer cytotoxicity of CAR-T cells comprising D4 against a pancreatic cancer cell line (PANC-1).

Figure 12:
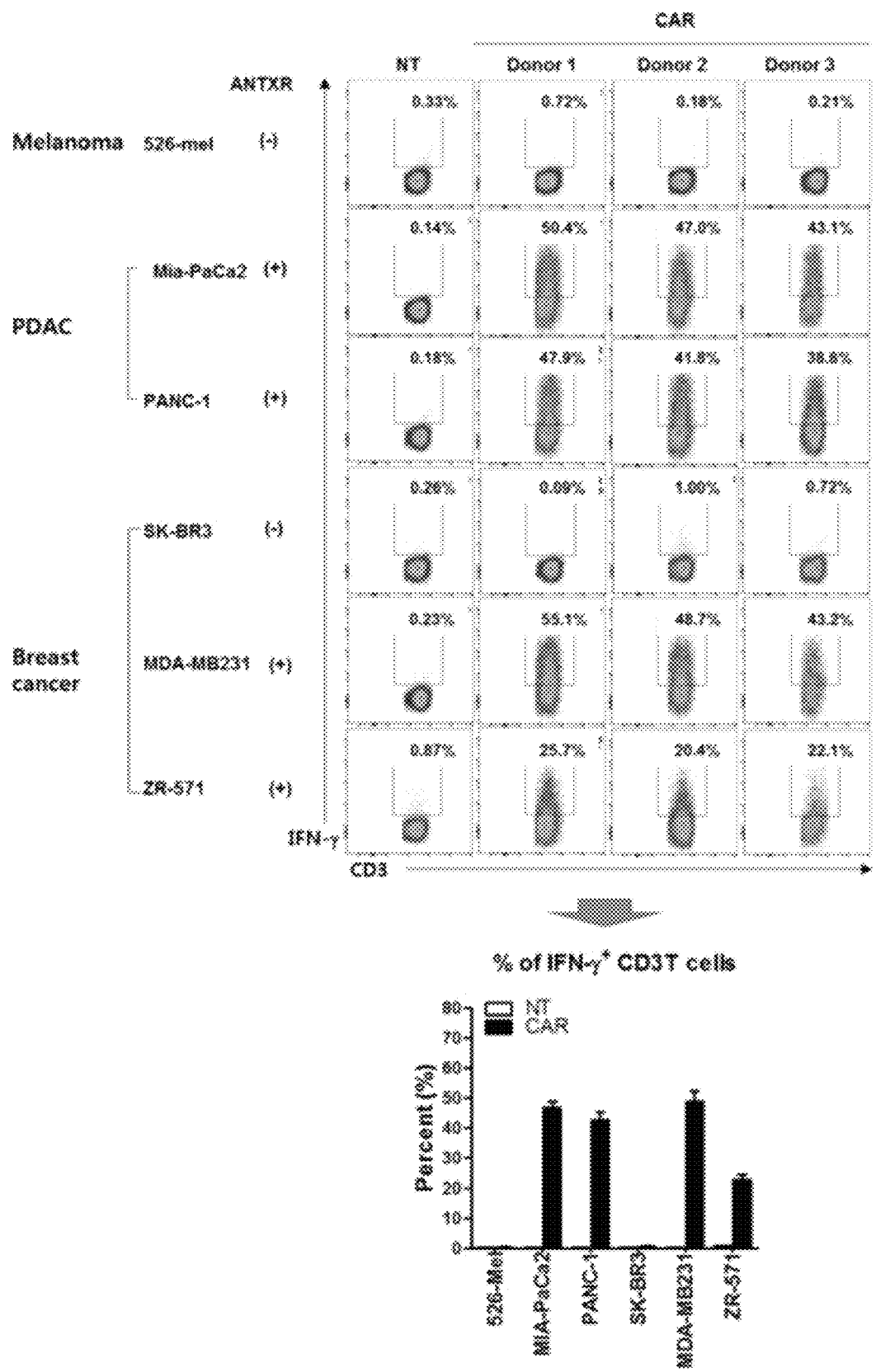

FIG. 12 shows the anticancer cytotoxicity and activity of CAR-T cells produced using T cells isolated from PBMC against melanoma (526-mel), pancreatic cancer (PANC-1, Mia-PaCa2), and breast cancer cell lines (SK-BR3, MDA-231, ZR-571).

Figure 13:
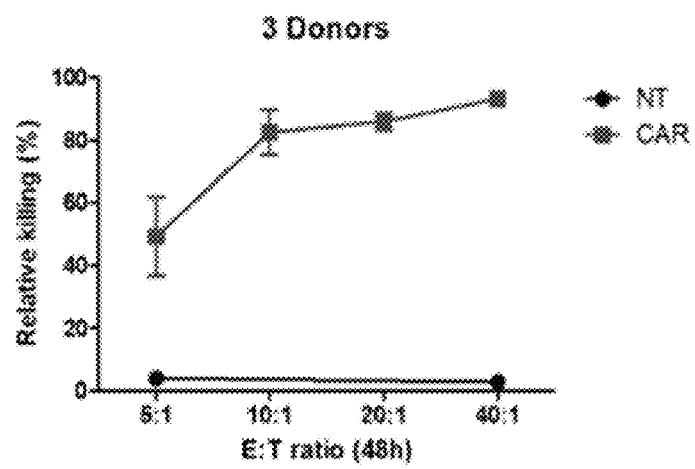

FIG. 13 is a graph showing the cytotoxicity of CAR-T cells produced using T cells isolated from PBMCs against a pancreatic cancer cell line (PANC-1_RFP).

Figure 14:
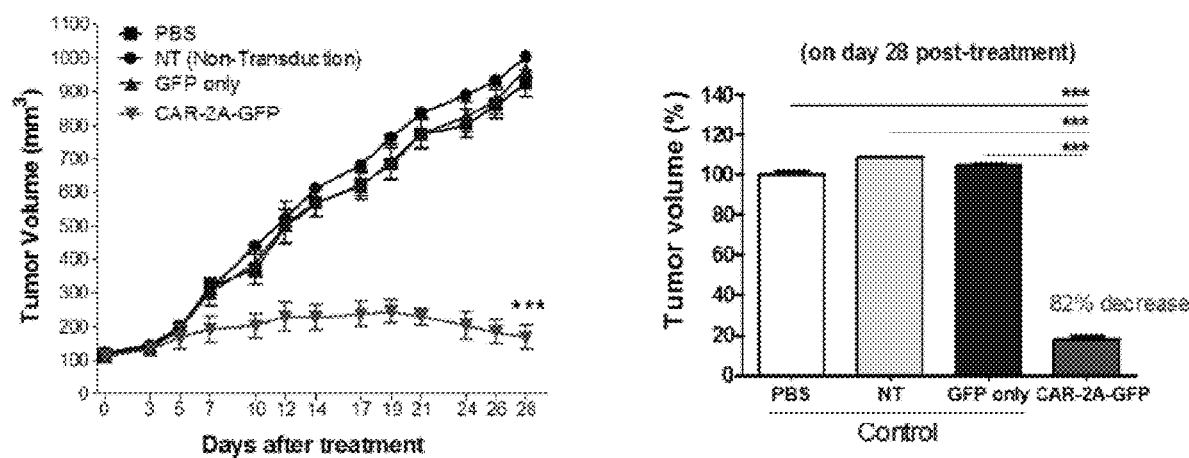

FIG. 14 is a graph showing the results of application of CAR-T cells produced using T cells isolated from PBMCs to an ANTXR-expressing pancreatic-cancer animal model.

4. DETAILED DESCRIPTION AND PREFERRED EMBODIMENTS OF THE INVENTION

Unless defined otherwise, all technical and scientific terms used herein have the same meanings as appreciated by those skilled in the field to which the present invention pertains. In general, the nomenclature used herein is well-known in the art and is ordinarily used.

As a result of extensive efforts to develop a novel chimeric antigen receptor for treating solid cancer, the present inventors found that ANTXR1 and ANTXR2 are expressed very little in normal tissues, and are specifically expressed only in pancreatic cancer tissues. In an embodiment of the present invention, gene changes in cancer tissues and IPMN tissues isolated from pancreatic cancer patients, along with normal pancreatic tissues, were analyzed using a microarray method, and 6 kinds of genes showing increased expression in pancreatic cancer tissues were selected (Table 1). Among the six primarily selected genes, only ANTXR1 and ANTXR2 satisfied all requirements, namely that the amount of expression of mRNA should satisfy the relationship "normal tissue <IPMN tissue <pancreatic ductal adenocarcinoma (PDAC) tissue", that proteins that are expressed should be present on the cell surface, and that the genes should be expressed very little in normal tissues. In addition, according to the present invention, the PA63 ligand specifically targeting ANTXR1 and ANTXR2 was identified, and a CAR specific to ANTXR1 or ANTXR2, which was engineered to comprise domain 4, which is indispensable for binding of the PA63 ligand to the receptor, or a fragment comprising the domain 4 as an extracellular binding domain, a hinge region and transmembrane domain derived from CD8α, a CD3ζ chain as a primary signaling domain, and CD28 and CD137 as co-stimulatory signaling domains, was developed.

Accordingly, in one aspect, the present invention is directed to a nucleic acid encoding a chimeric antigen receptor (CAR) comprising an extracellular binding domain, a transmembrane domain, and an intracellular signaling domain, wherein the extracellular binding domain recognizes an anthrax toxin receptor (ANTXR).

As used herein, the term "chimeric antigen receptor (CAR)" refers to a recombinant polypeptide construct that is engineered to impart the target cell and intracellular signaling to immune effector cells. CARs are molecules that are combined with T cell receptor-activated intracellular domains in order to produce chimeric proteins having antibody-based specificity for target antigens (e.g., tumor antigens) and anti-tumor-cell immune activity specific therefor. As used herein, the term "chimera" refers to an organism composed of distinct protein parts or DNA derived from different origins. The CAR comprises at least an extracellular binding domain, a transmembrane domain, and an intracellular signaling domain.

As used herein, the term "extracellular binding domain" refers to a portion of a CAR having the ability to specifically bind to a target antigen of interest. The extracellular binding domain may include any protein, polypeptide, oligopeptide or peptide that retains the ability to specifically recognize a biological molecule (e.g., a cell surface receptor, a tumor protein, lipid, polysaccharide, other cell surface target molecule, or a component thereof) and to bind thereto. The binding domain includes any naturally occurring, synthetic, semisynthetic or recombinantly produced counterpart for binding to the biological molecule of interest.

As used herein, the term "specifically binding" refers to binding of a molecule to another molecule with greater binding affinity than that of a background binding. For example, when the extracellular binding domain binds to or associates with the target molecule with an affinity of about $10^5$ $M^{-1}$ or Ka (i.e., the equilibrium dissociation constant of a specific binding interaction having a unit of 1/M) or more, it specifically binds thereto. Alternatively, affinity may be defined as an equilibrium dissociation constant (Kd) of a specific binding interaction having a unit of M (e.g., $10^{-5}$ M to $10^{-13}$ M or less).

The affinities of the extracellular binding domain and CAR according to the present invention can be easily measured by conventional techniques, such as binding, association or substitution analysis using competitive ELISA (enzyme-linked immunosorbent assay) or labeled ligands, or surface-plasmon resonance devices such as a Biacore T100 (commercially available from Biacore, Inc., Piscataway, New Jersey, USA), or optical biosensors such as EPIC systems and EnSpire, commercially available from Corning and Perkin Elmer, respectively.

In the present invention, the extracellular binding domain may recognize ANTXR. The extracellular binding domain that recognizes ANTXR may be an antibody, aptamer, or ligand that specifically binds to ANTXR, but is not limited thereto.

In the present invention, the ligand may be a PA63 ligand or a fragment thereof.

The PA63 ligand may be represented by the amino acid sequence of SEQ ID NO:1.

In addition, the fragment may be domain 4 of the PA63 ligand or a fragment comprising the domain 4.

The fragment comprising domain 4 of the PA63 ligand may be represented by the amino acid sequence of SEQ ID NO:2.

In the present invention, D1 is domain 1 of the PA63 ligand, D2 is domain 2 of the PA63 ligand, D3 is domain 3 of the PA63 ligand, and D4 is domain 4 of the PA63 ligand. D1+D4 is defined as a combination of domain 1 and domain 4 of the PA63 ligand, D2+D4 is defined as a combination of domain 2 and domain 4 of the PA63 ligand, D3+D4 is defined as a combination of domain 3 and domain 4 of the PA63 ligand, D4+D4 is defined as a combination of domain 4 and domain 4 of the PA63 ligand, D1+D2+D4 is defined as a combination of domain 1, domain 2 and domain 4 of the PA63 ligand, D2+D3+D4 is defined as a combination of domain 2, domain 3 and domain 4 of the PA63 ligand, D1+D3+D4 is defined as a combination of domain 1, domain 3 and domain 4 of the PA63 ligand, D4+D4+D1 is defined as a combination of domain 4, domain 4 and domain 1 of the PA63 ligand, D4+D4+D2 is defined as a combination of domain 4, domain 4 and domain 2 of the PA63 ligand, D4+D4+D3 is defined as a combination of domain 4, domain 4 and domain 3 of the PA63 ligand, D4+D4+D1+D2 is defined as a combination of domain 4, domain 4, domain 1 and domain 2 of the PA63 ligand, D4+D4+D1+D3 is defined as a combination of domain 4, domain 4, domain 1 and domain 3 of the PA63 ligand, D4+D4+D2+D3 is defined as a combination of domain 4, domain 4, domain 2 and domain 3 of the PA63 ligand, D4+D4+D4 is defined as a combination of domain 4, domain 4 and domain 4 of the PA63 ligand, D4+D4+D4+D1 is defined as a combination of domain 4, domain 4, domain 4 and domain 1 of the PA63 ligand, D4+D4+D4+D2 is defined as a combination of domain 4, domain 4, domain 4 and domain 2 of the PA63 ligand, D4+D4+D4+D3 is defined as a combination of domain 4, domain 4, domain 4 and domain 3 of the PA63 ligand, and D4+D4+D4+D4 is defined as a combination of domain 4, domain 4, domain 4 and domain 4 of the PA63 ligand.

The fragment comprising domain 4 of the PA63 ligand may be selected from the group consisting of D1+D4, D2+D4, D3+D4, D4+D4, D1+D2+D4, D2+D3+D4, D1+D3+D4, D4+D4+D1, D4+D4+D2, D4+D4+D3, D4+D4+D1+D2, D4+D4+D1+D3, D4+D4+D2+D3, D4+D4+D4, D4+D4+D4+D1, D4+D4+D4+D2, D4+D4+D4+D3 and D4+D4+D4+D4.

The fragment comprising domain 4 of the PA63 ligand may be selected from the group consisting of the amino acid sequences of SEQ ID NO:2 to SEQ ID NO:9.

In an embodiment of the present invention, D4-introduced CAR-T cells or D4+D4-introduced CAR-T cells have better cytotoxic effects than those of CAR-T cells comprising the PA63 ligand.

As used herein, the term "PA63" refers to a truncated 63 kDa portion of a protective antigen (PA, 83 kDa), which is an anthrax toxin protein. The anthrax toxin is secreted by *Bacillus anthracis*, which is a gram-positive bacterium.

In general, the pathogenicity of anthrax is known to be determined by toxin-producing ability and capsular formation. Proteins that affect the toxin-producing ability of anthrax include protective antigens (PA), edema factors (EF), and lethal factors (LF). None of these exhibits toxicity alone, but protective antigens and edema factors combine together to form edema toxins (EdTx), and protective antigens and lethal factors combine together to form lethal toxins (LeTx).

The PA binds to the receptor protein (anthrax toxin receptor) on the surface of infectious cell lines such as macrophages, and is then cleaved into PA20 (20 kDa) and PA63 (63 kDa) by furin family protease. It is known that among these, PA63 becomes a heptamer, binds to LF or EF, and acts as a toxin delivery channel that transports the same into cells.

Such a complex enters cells through an endocytosis mechanism. When the pH of the endosome is lowered, the PA63 heptamer is structurally changed, and pores are formed in the endosomal membrane. As a result, LF or EF is released into the cytoplasm, which thus becomes toxic (Jiang J. Atomic structure of anthrax protective antigen pore elucidates toxin translocation. Nature. 2015).

In an embodiment of the present invention, a CAR introduced with a nucleic acid encoding D4 and a CAR introduced with a nucleic acid encoding D4+D4 were constructed, and whether or not CAR-T cells produced by introducing the CAR into T cells exhibit efficacy for treating pancreatic cancer was determined. The CAR-T cells introduced with the nucleic acid encoding D4 or D4+D4 had better efficacy for treating pancreatic cancer than the CAR-T cells introduced with nucleic acid encoding the PA63 ligand.

Thus, it will be apparent to those skilled in the art that all of the cases in which a CAR is constructed by introducing a nucleic acid encoding D1+D4, D2+D4, D3+D4, D4+D4, D1+D2+D4, D2+D3+D4, D1+D3+D4, D4+D4+D1, D4+D4+D2, D4+D4+D3, D4+D4+D1+D2, D4+D4+D1+D3, D4+D4+D2+D3, D4+D4+D4, D4+D4+D4+D1, D4+D4+D4+D2, D4+D4+D4+D3 or D4+D4+D4+D4 can exhibit identical or similar effects thereto.

In the present invention, the ANTXR may be ARTXR1 (anthrax toxin receptor 1) or ARTXR2 (anthrax toxin receptor 2).

The term "ANTXR1 (anthrax toxin receptor 1)" as used herein means an extracellular matrix protein, and is also called "TEM8 (tumor endothelial marker 8)". The specific nucleic acid sequence thereof can be seen from NCBI (NCBI Reference Sequence: NM_032208.2).

The term "ANTXR2 (anthrax toxin receptor 2)" as used herein means a protein involved in angiogenesis, and is also called "CMG2 (capillary morphogenesis gene 2)". The specific nucleic acid sequence thereof can be seen from NCBI (NCBI Reference Sequence: NM_058172.5).

In addition, in the present invention, the affinity of ANTXR1 and ANTXR2 with the PA63 ligand is Kd of 170 to 780 Pm, which is much higher than the affinity (Kd of 1 nM) of the antibodies used for ROR1, EGFR, and Her2/neu, which are previously developed CAR-T cell therapeutics (Karl A. (2010) Nature precedings 5221:1; Heather MS (2005) Curr. Opin. Microbiol. 8:106-112).

As used herein, the term "transmembrane domain" refers to a portion of a CAR that fuses an extracellular binding domain with an intracellular signaling domain and fixes the CAR to the plasma membrane of an immune effector cell. The transmembrane domain may be derived from natural, synthetic, semisynthetic, or recombinant sources. In the present invention, the transmembrane domain is selected from the group consisting of an alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, and CD154, but is not limited thereto.

In addition, the transmembrane domain may be attached to the extracellular binding domain of the CAR through a linker. For example, the linker may be a short oligo- or polypeptide linker having a length of 2 to 10 amino acids, and is preferably a glycine (G)-serine (S) doublet, but is not limited thereto. In the present invention, the CAR may comprise G4S1 (GGGGS), represented by the amino acid sequence of SEQ ID NO:10, as a linker.

The binding domain of the CAR is generally followed by at least one "hinge domain" As used herein, the term "hinge domain" refers to a portion of a CAR which is spaced apart from the surface of the effector cell and plays a key role in the positioning of the antigen-binding domain to enable appropriate cell/cell contact, antigen binding, and activation. The CAR generally comprises at least one hinge domain between the extracellular binding domain and the transmembrane domain. The hinge domain may be derived from natural, synthetic, semi-synthetic, or recombinant sources. The hinge domain may include the amino acid sequence of a naturally occurring immunoglobulin hinge region or a modified immunoglobulin hinge region. The term "modified hinge region" refers to (a) a naturally occurring hinge region in which up to 30% of amino acids are modified (e.g., up to 25%, 20%, 15%, 10% or 5% of amino acids are substituted or deleted), (b) a portion of a naturally occurring hinge region having at least 10 amino acids (e.g. at least 12, 13, 14 or 15 amino acids) in length in which up to 30% of the amino acids are modified (e.g., up to 25%, 20%, 15%, 10% or 5% of amino acids are substituted or deleted), or (c) a portion of a naturally occurring hinge region including a core hinge region (4, 5, 6, 7, 8, 9, 10, 11, 12, 13, 14 or 15, or at least 4, 5, 6, 7, 8, 9, 10, 11, 12, 13, 14 or 15 amino acids in length). In certain embodiments, at least one cysteine residue in the naturally occurring immunoglobulin hinge region may be substituted with at least one other type of amino acid residue (e.g., at least one serine residue). The modified immunoglobulin hinge region may alternatively or additionally have a proline residue of a wild-type immunoglobulin hinge region substituted with another amino acid residue (e.g., a serine residue). The hinge domain may include a hinge region derived from the extracellular region of type-1 membrane proteins such as CD8α, CD4, CD28 and CD7, and may be a wild-type hinge region from these molecules or a hinge region modified therefrom.

In the present invention, the transmembrane domain bound by a linker may be encoded by the nucleic acid sequence of SEQ ID NO:11 derived from CD8α, but is not limited thereto.

In the present invention, the transmembrane domain comprising the hinge domain may be encoded by the nucleic acid sequence of SEQ ID NO:15, derived from CD8α, but is not limited thereto.

As used herein, the term "intracellular signaling domain" refers to a portion of a CAR that is involved in effector cell functions such as activation including the release of cytotoxic factors to CAR-bound target cells, cytokine production, proliferation and cytotoxic activity, or effective delivery of a message of CAR binding to a target antigen into the immune effector cells, in order to induce other cellular responses caused by antigen binding to the extracellular binding domain of the CAR. The effector function refers to a specific function of a cell. For example, the effector function of T cells may be cytolytic activity, may be activity including the secretion of cytokines, or may facilitate such activity. Thus, the intracellular signaling domain means a portion of a protein that transmits an effector function signal and directs the cell to perform a specific function.

It is known that a signal generated by the T-cell receptor alone cannot sufficiently activate T cells, and thus a co-stimulatory signal is further required. Thus, T cell activation is mediated by two different intracellular signaling domains. For example, T cell activation is mediated by a primary signaling domain, which initiates antigen-dependent primary activation through a T-cell receptor, and a co-stimulatory signaling domain, which acts in an antigen-independent manner to provide a secondary signal. Accordingly, in the present invention, the intracellular signaling domain may include the "primary signaling domain" and the "co-stimulatory signaling domain".

As used herein, the term "primary signaling domain" refers to a signaling domain that regulates the primary activation of a T-cell receptor complex in a stimulatory or suppressive manner. The primary signaling domain acting in the stimulatory manner may contain a signaling motif known as immunoreceptor tyrosine-based activation motif or ITAM. The ITAM containing the primary signaling domain may be selected from the group consisting of TCRζ, FcRγ, FcRβ, CD3γ, CD3δ, CD3ε, CD3ζ; CD22, CD79a, CD79b and CD66d, but is not limited thereto.

In the present invention, the primary signaling domain may be CD3, encoded by the nucleic acid sequence of SEQ ID NO:12 or SEQ ID NO:16, but is not limited thereto.

As used herein, the term "co-stimulatory signaling domain" refers to an intracellular signaling domain of a co-stimulatory molecule. The co-stimulatory molecule is a cell surface molecule other than an Fc receptor which provides secondary signals required for efficient activation and functions of T lymphocytes upon binding to an antigen receptor or antigen. In the present invention, the co-stimulatory signaling domain is selected from the group consisting of OX40, CD2, CD27, CD28, CDS, ICAM-1, LFA-1 (CD11a/CD18), ICOS (CD278) and 4-1BB (CD137), but is not limited thereto.

In the present invention, the co-stimulatory signaling domain may be CD28, encoded by the nucleic acid sequence of SEQ ID NO:13 or SEQ ID NO:17, and CD137, encoded by the nucleic acid sequence of SEQ ID NO:14 or SEQ ID NO:18, but is not limited thereto.

Upon designing the CAR according to the present invention, a nucleic acid encoding a signal peptide may be inserted in front of the PA63 ligand or fragment thereof. The signal peptide may be GM-CSF, CD8 alpha signal peptide, or the like, but GM-CSF is most often used in CAR engineering, and GM-CSF was used as the signal peptide in the embodiment of the present invention.

In another aspect, the present invention is directed to a vector comprising the nucleic acid encoding the chimeric antigen receptor.

As used herein, the term "vector" refers to a nucleic acid molecule capable of transferring or transporting another nucleic acid molecule. The transferred nucleic acid is generally linked to a vector nucleic acid molecule, and is, for example, inserted into the vector nucleic acid molecule. The vector may include sequences directing autonomous replication in cells, or may include sequences sufficient to enable integration into the host cell DNA. The vector may be selected from the group consisting of DNA, RNA, plasmids, lentiviral vectors, adenovirus vectors, and retroviral vectors, but is not limited thereto. The vector is preferably a pMSCV vector, which is a retroviral vector, but is not limited thereto.

In another aspect, the present invention is directed to a recombinant cell comprising the vector.

As used herein, the term "recombinant cell" refers to a cell that is genetically modified to express the CAR of the present invention for use in the treatment of cancer or the like. The term "genetically modified" means the addition of foreign genetic material in the form of DNA or RNA to the total genetic material of a cell.

In the present invention, the cells may be T cells or NK cells. Therefore, the recombinant cell comprising the vector which comprises the nucleic acid encoding the CAR according to the present invention is a CAR-T cell (chimeric antigen receptor T cell) or CAR-NK cell (chimeric antigen receptor natural killer cell).

In the present invention, the T cell is selected from the group consisting of cytotoxic T lymphocytes (CTLs), tumor-infiltrating lymphocytes (TILs), and T cells isolated from peripheral blood mononuclear cells (PBMCs).

Preferably, the cell may be a human CD8+ T cell, and the cell used in the examples of the present invention may be a NYESO-1 T cell, but is not limited thereto.

In another aspect, the present invention is directed to a pharmaceutical composition for preventing or treating solid cancer comprising the recombinant cell.

In another aspect, the present invention is directed to a method of preventing or treating solid cancer comprising administering the recombinant cell to a subject.

In another aspect, the present invention is directed to the use of the recombinant cell for the prevention or treatment of solid cancer.

In another aspect, the present invention is directed to the use of the recombinant cell for the preparation of a therapeutic agent for preventing or treating solid cancer.

As used herein, the term "prevention" refers to any action that inhibits or delays the progression of solid cancer through administration of the composition of the present invention, and the term "treatment" refers to suppression of the onset of solid cancer or alleviation or elimination of symptoms of solid cancer.

In one embodiment of the present invention, anticancer cytotoxicity of CAR-T cells against pancreatic cancer cells was found, but the present invention is not limited thereto.

It will be apparent to those skilled in the art that, according to the mechanism of cytotoxic action of PA63, the domain 4 of the PA63 ligand or the fragment comprising domain 4 according to the present invention may specifically bind not only to pancreatic cancer cells or tissues, but also to other cancer cells or tissues expressing ANTXR, and CAR-containing cells comprising domain 4 of the PA63 ligand or the fragment comprising domain 4 according to the present invention have a cytotoxic effect against cancer expressing ANTXR.

In one embodiment of the present invention, it was confirmed that the cytotoxic effect of CAR-T cells comprising the fragment having domain 4 of the PA63 ligand was superior to the effect of the CAR-T cells comprising the PA63 ligand.

As used herein, the term "solid cancer" refers to a tumor that is composed of blood vessels or connective tissues and thus has a predetermined hardness and shape, and is, for example, pancreatic cancer, stomach cancer, colon cancer, lung cancer, breast cancer, germ cell cancer, liver cancer, skin cancer, bladder cancer, prostate cancer, uterine cancer, cervical cancer, ovarian cancer, or the like, but is not limited thereto.

In the present invention, the solid cancer may be pancreatic cancer, gastric cancer, colon cancer, lung cancer, breast cancer, germ cell cancer, liver cancer, skin cancer, bladder cancer, prostate cancer, uterine cancer, cervical cancer, or ovarian cancer that expresses ANTXR (anthrax toxin receptor), but is not limited thereto, and the ANTXR includes ANTXR1 or ANTXR2.

As used herein, the term "pancreatic cancer" refers to a tumor composed of cancer cells formed in the pancreas. In general, pancreatic ductal cancer, originating in pancreatic duct cells, accounts for about 90% of pancreatic cancer. More than 85% of pancreatic duct cells have a point mutation in the K-ras gene, which is activated upon the occurrence of pancreatic cancer (Li et al. (2004) Lancet 363:1049-1057; Xiong (2004) Cancer Chem Pharm 54: S69-77). For early treatment of pancreatic cancer, it is necessary to understand precancerous lesions and progression of cancer in the pancreas, and the prognosis according to the stage or size of the cancer. Known representative precancerous lesions of the pancreas include pancreatic intraepithelial neoplasia (PanIN), intraductal papillary mucinous neoplasm (IPMN), mucinous cystic neoplasm (MCN), and the like (Hruban R. H., (2001) Am. J. Surg. Pathol. 25: 579-586; Ottenhof N. A., (2009) Arch. Pathol. Lab. Med. 133: 375-381; Sipos B., (2009) Pancreatology 9: 45-54). In particular, IPMN has recently been found with increasing frequency due to the improved resolution of various medical diagnostic imaging systems and increased frequency of health check-ups. IPMN is attracting a great deal of interest because it is a progenitor lesion of pancreatic cancer, in which benign tumors may gradually progress into malignant tumors, and the frequency of pancreatic cancer accompanying such a lesion is high, even in areas far from the lesion.

The pharmaceutical composition for preventing or treating solid cancer may further comprise a pharmaceutically acceptable carrier.

As used herein, the term "pharmaceutically acceptable carrier" refers to a carrier or diluent that does not impair the biological activities or properties of the administered compound and does not irritate an organism. Pharmaceutically acceptable carriers for compositions formulated into liquid solutions are sterilized and biocompatible, and examples thereof include saline, sterile water, buffered saline, albumin injection solutions, dextrose solutions, maltodextrin solutions, glycerol, and mixtures of one or more thereof. If necessary, other ordinary additives such as antioxidants, buffers and bacteriostatic agents may be added. In addition, the composition may be formulated into injectable solutions such as aqueous solutions, suspensions and emulsions, pills, capsules, granules, or tablets by further adding diluents, dispersants, surfactants, binders and lubricants.

The pharmaceutical composition according to the present invention may be any one of various oral or parenteral formulations. In this regard, the pharmaceutical composition may be formulated using an ordinary diluent or excipient such as a filler, a thickener, a binder, a wetting agent, a disintegrant, a surfactant, or the like. Solid formulations for oral administration may include tablets, pills, powders, granules, capsules, and the like. Such a solid formulation is prepared by mixing at least one compound with at least one excipient such as starch, calcium carbonate, sucrose, lactose, or gelatin. In addition to a simple excipient, a lubricant such as magnesium stearate or talc may be used. Liquid formulations for oral administration may include suspensions, oral liquids, emulsions, syrups, and the like. In addition to a simple diluent such as water or liquid paraffin, various excipients such as wetting agents, sweeteners, aromatics, and preservatives may be incorporated in the liquid formulations. In addition, formulations for parenteral administration include sterile aqueous solutions, non-aqueous solvents, suspensions, emulsions, lyophilizates, suppositories, and the like. Useful non-aqueous solvents and suspension solvents include propylene glycol, polyethylene glycol, vegetable oils such as olive oil, and injectable esters such as ethyl oleate. The basic ingredients of suppositories include Witepsol, macrogol, Tween 61, cacao butter, laurin butter, glycerogelatin and the like.

Suitable pharmaceutically acceptable carriers and formulations are described in detail in Remington's Pharmaceutical Science ($17^{th}$ ed., 1995).

The composition of the present invention may be administered orally or parenterally, and the parenteral administration may be intravenous injection, subcutaneous injection, intramuscular injection, intraperitoneal injection, endothelial administration, topical administration, intranasal administration, intrapulmonary administration, rectal administration, or the like. Upon oral administration, proteins or peptides are digested. Thus, an oral composition may be coated with an active drug or may be formulated so as to prevent the same from being degraded in the stomach. In addition, the composition may be administered using any device capable of delivering the active substance to target cells.

The suitable dose of the pharmaceutical composition for preventing or treating solid cancer may vary depending on factors such as the formulation method, administration method, and age, body weight, gender, pathological conditions, diet, administration time, administration route, excretion rate, and responsiveness of the patient. A dose effective for the desired treatment or prophylaxis can be easily determined and prescribed by a skilled physician.

The composition of the present invention may be administered as a single therapeutic agent or in combination with another therapeutic agent, and may be administered sequentially or simultaneously with a conventional therapeutic agent.

Hereinafter, the present invention will be described in more detail with reference to examples. However, it will be obvious to those skilled in the art that these examples are provided only for illustration of the present invention, and should not be construed as limiting the scope of the present invention.

5. EXAMPLES

Example 1: Identification of Genes Specific to Solid Cancer

In order to identify a gene specific for solid cancer, tissues related to pancreatic cancer as solid cancer were used. Pancreatic cancer tissues isolated from a total of 104 pancreatic cancer patients including 3 pancreatic cancer patients in stage 1, 89 in stage 3, and 12 in stage 4 were prepared. Then, gene changes in cancer tissue, IPMN tissue, and normal pancreatic tissue were analyzed using a microarray, and 6 kinds of genes showing increased expression in pancreatic cancer tissue were selected (Table 1).

TABLE 1

| | | IPMN/normal | | PDAC/IPMN | | PDAC/normal | |
|---|---|---|---|---|---|---|---|
| | Gene | change in expression amount | q-value | change in expression amount | q-value | change in expression amount | q-value |
| 1 | ANTXR1 | 1.26509 | 15.4246 | 1.97897 | 0 | 2.55661 | 0 |
| 2 | ANTXR2 | 1.40985 | 0.335413 | 1.18386 | 16.605 | 1.68669 | 0 |
| 3 | TMC5 | 3.33643 | 0 | 47.9433 | 20.737 | 2.97206 | 0 |
| 4 | CLDN18 | 7.86426 | 0 | 0.364816 | 0 | 2.97039 | 0 |
| 5 | MUC13 | 5.46988 | 0 | 0.502169 | 0 | 2.71774 | 0 |
| 6 | MMP14 | 1.4564 | 0.133632 | 1.7475 | 0 | 2.5949 | 0 |

Genes that satisfied all three of the following requirements were further selected from among the six primarily selected genes.

1) genes having mRNA expression levels that satisfy "normal tissue <IPMN tissue <pancreatic cancer (PDAC) tissue"

Figure 1:
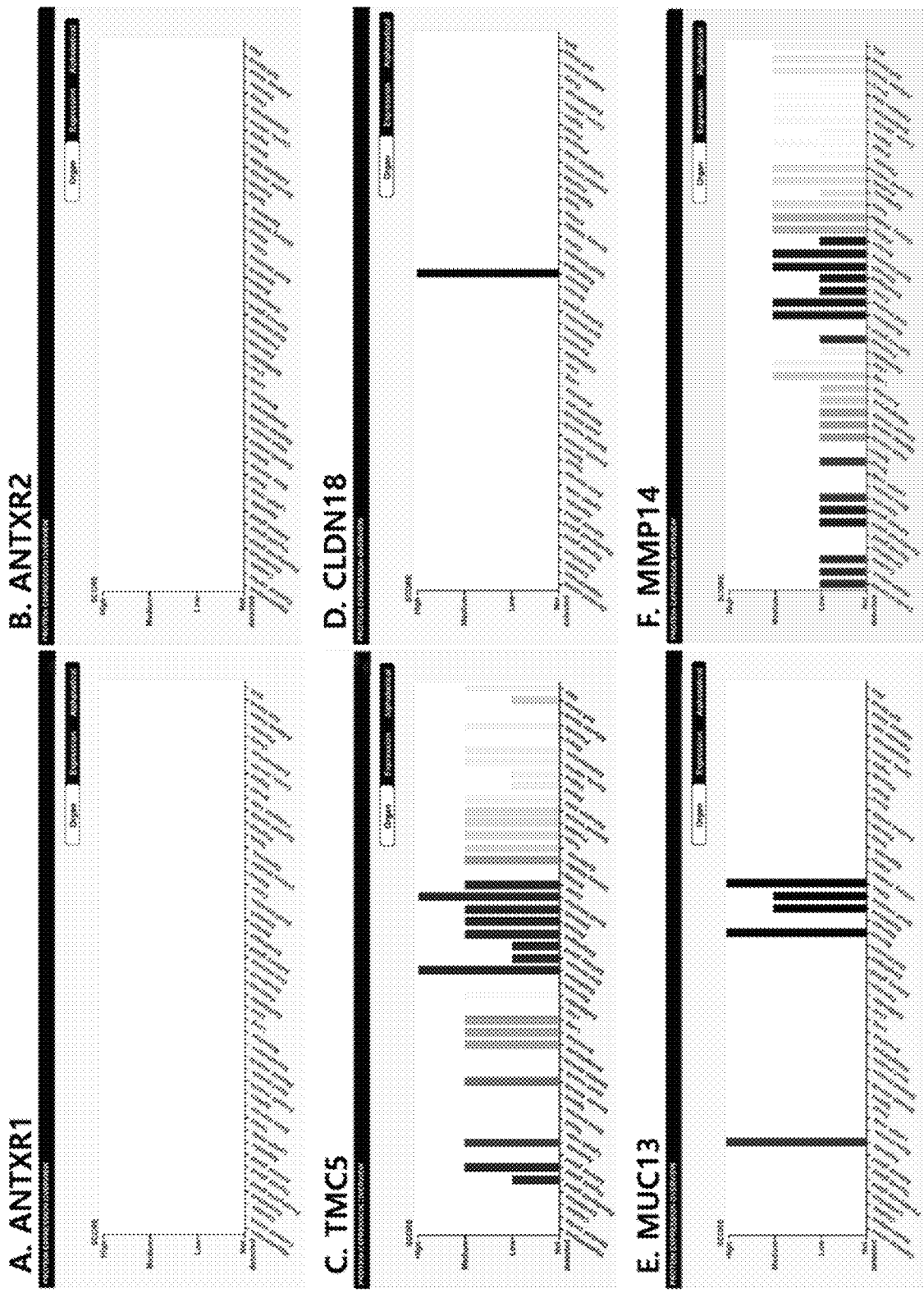

2) genes in which the expressed protein is present on the cell surface 3) genes with little expression in normal tissues FIG. 1 shows the protein expression levels of six primarily selected genes in normal tissues, wherein A shows the protein expression level of ANTXR1 (anthrax toxin receptor 1), B shows the protein expression level of ANTXR2 (anthrax toxin receptor 2), C shows the protein expression level of TMC5 (transmembrane channel-like 5), D shows the protein expression level of CLDN18 (claudin-18), E shows the protein expression level of MUC13 (Mucin 13), and F shows the protein expression level of MMP14 (matrix metallopeptidase 14).

All of the six primarily selected genes are expressed on the cell surface and satisfy the above requirements 1) and 2). However, as can be seen in FIG. 1, four genes, excluding ANTXR1 and ANTXR2, are also expressed in normal tissues, and thus ANTXR1 and ANTXR2 were the only genes satisfying all three requirements (FIG. 1).

In order to further detect the actual expression of ANTXR1 and ANTXR2, real-time RT-PCR (RT-PCR) was performed using peripheral blood mononuclear cells (PBMCs), primary pancreatic cancer tissues, and pancreatic cancer cell lines. PBMC was used as a negative control, and PANC-1 was used as a positive control. Specifically, total RNA was extracted using TRIzol/chloroform. After mRNA amplification, cDNA was produced using reverse transcriptase. The primers of Table 2 were added, and the mRNA expression amounts of ANTXR1 and ANTXR2 were detected using real-time RT-PCR. Analysis was performed using a StepOnePlus Real-Time PCR system (Applied Biosystems) and iTaq universal SYBR Green Supermix (Biorad). The concentration of cDNA was 0.5 µg/µl, and each primer was used in a concentration of 10 pM. Denaturation at 95° C. for 15 minutes and annealing/extension at 60° C. for 60 seconds, respectively, were performed in 40 cycles.

TABLE 2

|  | Forward | Reverse |
| --- | --- | --- |
| ANTXR1 | TGCTGCACCACTGGAAT GAAATC (SEQ ID NO: 24) | CTCCTCCTGGCAGAACT TTCTGG (SEQ ID NO: 25) |
| ANTXR2 | CTTTCATTGTGTTTTCT TCTCAAGCAAC (SEQ ID NO: 26) | GTTTTCAAGCCTCCTGC TTTCTGAAT (SEQ ID NO: 27) |

Figure 2:
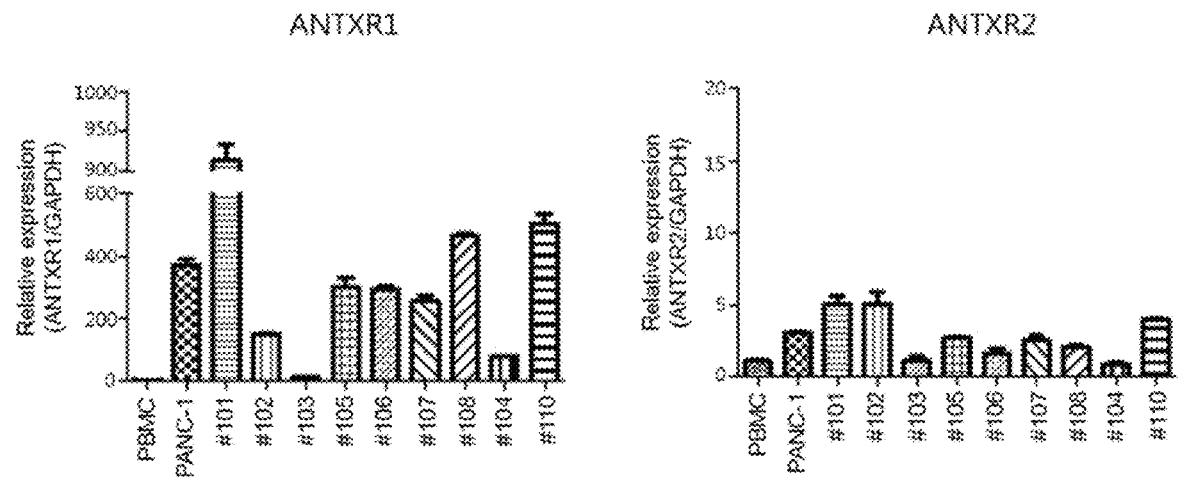

The result showed that ANTXR1 and ANTXR2 mRNA expression was remarkably increased in primary pancreatic cancer tissues (FIG. 2). In addition, the result of analysis of HUVEC cells (normal cells), MDA-MB 231 cells, and pancreatic cancer cell lines (AsPC1, Capan2, PANC1, Mia-PaCa2, SNU-213, SNU-324, SNU-2466, SNU-2469, SNU-2485, SNU-2543) showed that ANTXR1 and ANTXR2 mRNA expression increased in pancreatic cancer cell lines.

Figure 3:
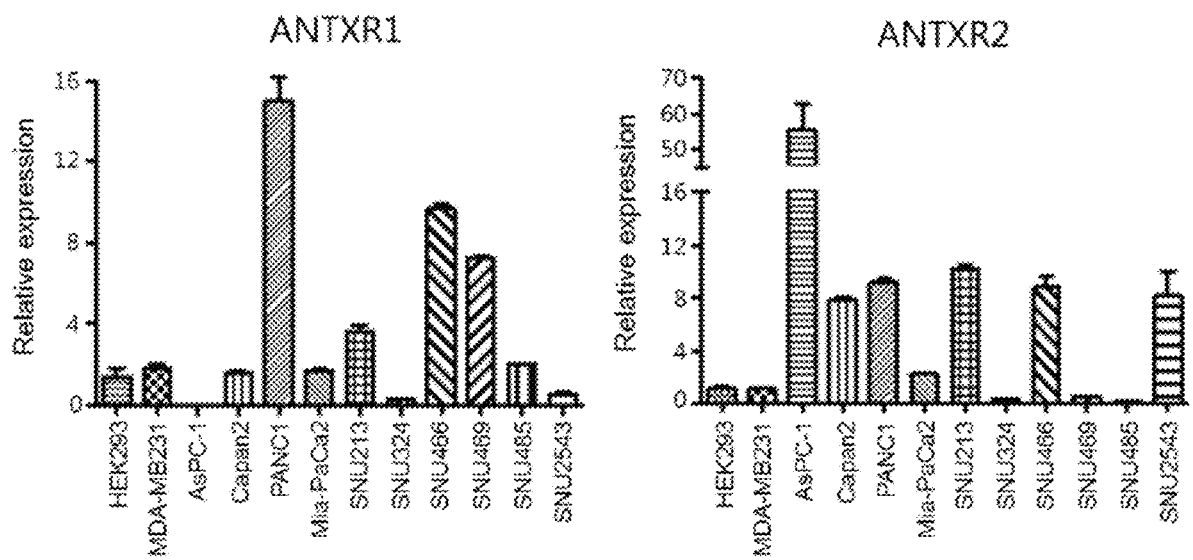
FIG. 3 shows the expression levels of ANTXR1 and ANTXR2 mRNA analyzed through RT-PCR (real-time RT-PCR) in normal cells (HEK-293 cells), MDA-MB 231 cells, and pancreatic cancer cell lines (AsPC1, Capan2, PANC1, Mia-PaCa2, SNU-213, SNU-324, SNU-2466, SNU-2469, SNU-2485, and SNU-2543).

In particular, ANTXR1 mRNA expression remarkably increased in SNU-2466 and SNU-2469, and ANTXR2 mRNA expression remarkably increased in AsPC1 (FIG. 3).

Figure 4:
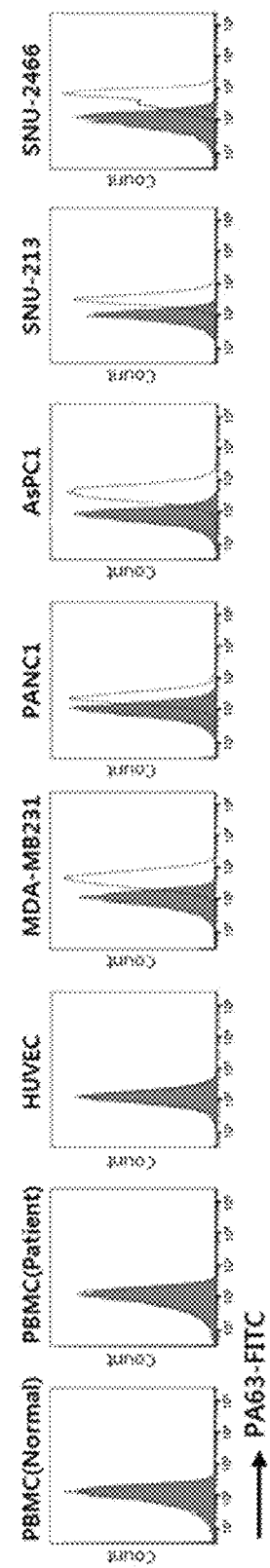
FIG. 4 shows the expression levels of ANTXR1 and ANTXR2 proteins on the cell surface of normal cells (HEK-293 cells), MDA-MB-231 cells, and pancreatic cancer cell lines (AsPC1, PANC1, SNU-213, SNU-2466) analyzed using flow cytometry.

In addition, the result of analysis of expression levels of ANTXR1 and ANTXR2 proteins on the cell surface of normal cells (HUVEC cells), MDA-MB-231 cells, and pancreatic cancer cell lines (AsPC1, PANC1, SNU-213, SNU-2466) using flow cytometry showed that the expression of ANTXR1 and ANTXR2 proteins increased (FIG. 4).

In addition, after treatment with a reagent conjugated with FITC exhibiting fluorescence in PA63 which is a ligand of ANTXR1 and ANTXR2, the expression levels of cell surface proteins ANTXR1 and ANTXR2 were indirectly detected again in normal cells (HUVEC cells), MDA-MB 231 cells, and pancreatic cancer cell lines (AsPC1, Capan2, PANC1, Mia-PaCa2, SNU-213, SNU-324, SNU-2466, SNU-2469, SNU-2485 and SNU-2543) found to have remarkably increased expression of ANTXR1 and ANTXR2 mRNA, using flow cytometry, and then the binding of PA63 to ANTXR1 and ANTXR2 was also detected (FIG. 5).

Example 2: ANTXR-Specific CAR Design and Construction

CARs specific for ANTXR1 or ANTXR2 were designed to include an extracellular binding domain, a transmembrane domain derived from CD8α, a G4S1 (GGGGS) linker or hinge region, a primary signaling domain of a CD3ζ chain, and CD28 and CD137 as co-stimulatory signaling domains.

A CAR introduced with the PA63 ligand as the extracellular binding domain was designed, and the vector shown in FIG. 6A was produced.

In addition, a CAR introduced with D4, D1+D4, D2+D4, D3+D4, D4+D4, D1+D2+D4, D2+D3+D4 or D1+D3+D4 was designed to include D4, which is essential for receptor binding of the PA63 ligand as the extracellular binding domain, and was then introduced at the PA63 site of the vector shown in FIG. 6B to produce a vector. In addition, the CAR was designed to include a nucleic acid encoding a signal peptide in front of the D4, D1+D4, D2+D4, D3+D4, D4+D4, D1+D2+D4, D2+D3+D4, or D1+D3+D4.

The signal peptide has a short amino acid sequence, and plays a key role in transporting the synthesized protein to the ER. When the protein arrives at the ER, the signal peptide is removed, and the protein is transported to the Golgi complex through a carrier. Then, proteins to be expressed on cell membranes rather than intracellular organelles must be transported to the destination. In this example, GM-CSF was used as the signal peptide for transporting the synthesized protein to the destination.

A nucleic acid encoding copGFP was introduced into the vector of FIG. 6B to detect the expression of CAR, but this may be omitted when actually using the CAR as an therapeutic agent.

Table 3 shows the sequences required for the production of a CAR including the PA63 ligand, and Table 4 shows the sequences required for the production of a CAR including a fragment of the PA63 ligand.

TABLE 3

| CAR portion | CAR of present invention | | Amino acid or nucleic acid sequence | SEQ ID NO. |
|---|---|---|---|---|
| Extracellular binding domain | PA63 ligand | | STSAGPTVPDRDNDGIPDSLEVEGYTVDVKNKR TFLSPWISNIHEKKGLTKYKSSPEKWSTASDPYS DFEKVTGRIDKNVSPEARHPLVAAYPIVHVDME NIILSKNEDQSTQNTDSQTRTISKNTSTSRTHTSE VHGNAEVHASFFDIGGSVSAGFSNSNSSTVAIDH SLSLAGERTWAETMGLNTADTARLNANIRYVNT GTAPIYNVLPTTSLVLGKNQTLATIKAKENQLSQ ILAPNNYYPSKNLAPIALNAQDDFSSTPITMNYN QFLELEKTKQLRLDTDQVYGNIATYNFENGRVR VDTGSNWSEVLPQIQETTARIIFNGKDLNLVERRI AAVNPSDPLETTKPDMTLKEALKIAFGFNEPNG NLQYQGKDITEFDFNFDQQTSQNIKNQLAELNA TNIYTVLDKIKLNAKMNILIRDKRFHYDRNNIAV GADESVVKEAHREVINSSTEGLLLNIDKDIRKILS GYIVEIEDTEGLKEVINDRYDMLNISSLRQDGKT FIDFKKYNDKLPLYISNPNYKVNVYAVTKENTII NPSENGDTSTNGIKKILIFSKKGYEIG | 1 |
| Linker | G4S1 | | GGGGS GGGGS GGGGS GGGGS GGGGS | 10 |
| Transmembrane domain | CD8α | | ACCACGACGCCAGCGCCGCGACCACCAACAC CGGCGCCCACCATCGCGTCGCAGCCCCTGTCC CTGCGCCCAGAGGCGTGCCGGCCAGCGGCGG GGGGCGCAGTGCACACGAGGGGGCTGGACTT CGCCTGTGATATCTACATCTGGGCGCCCTTGG CCGGGACTTGTGGGGTCCTTCTCCTGTCACTG GTTATCACC | 11 |
| Intracellular signaling domain | Primary signaling domain | CD3ζ | CTGAGAGTGAAGTTCAGCAGGAGCGCAGACG CCCCCGCGTACCAGCAGGGCCAGAACCAGCTC TATAACGAGCTCAATCTAGGACGAAGAGAGG AGTACGATGTTTTGGACAAGAGACGTGGCCGG GACCCTGAGATGGGGGGAAAGCCGAGAAGGA AGAACCCTCAGGAAGGCCTGTACAATGAACTG CAGAAAGATAAGATGGCGGAGGCCTACAGTG AGATTGGGATGAAAGGCGAGCGCCGGAGGGG CAAGGGGCACGATGGCCTTTACCAGGGTCTCA GTACAGCCACCAAGGACACCTACGACGCCCTT CACATGCAGGCCCTGCCCCCTCGCTA | 12 |
| | Co-stimulatory signaling domain | CD28 | TTTTGGGTGCTGGTGGTGGTTGGTGGAGTCCT GGCTTGCTATAGCTTGCTAGTAACAGTGGCCT TTATTATTTTCTGGGTGAGGAGTAAGAGGAGC AGGCTCCTGCACAGTGACTACATGAACATGAC TCCCCGCCGCCCCGGGCCCACCCGCAAGCATT ACCAGCCCTATGCCCCACCACGCGACTTCGCA GCCTATCGCTCC | 13 |
| | | CD137 | AAACGGGGCAGAAAGAAACTCCTGTATATATT CAAACAACCATTTATGAGACCAGTACAAACTA CTCAAGAGGAAGATGGCTGTAGCTGCCGATTT CCAGAAGAAGAAGAAGGAGGATGTGAACTG | 14 |

TABLE 4

| CAR portion | CAR of present invention | Amino acid or nucleic acid sequence | SEQ ID NO. |
|---|---|---|---|
| Extracellular binding domain | D4 | FHYDRNNIAVGADESVVKEAHREVINSSTEGLLLNID KDIRKILSGYIVEIEDTEGLKEVINDRYDMLNISSLRQD GKTFIDFKKYNDKLPLYISNPNYKVNVYAVTKENTIIN PSENGDTSTNGIKKILIFSKKGYEIG | 2 |
| | D1 + D4 | STSAGPTVPDRDNDGIPDSLEVEGYTVDVKNKRTFLSP WISNIHEKKGLTKYKSSPEKWSTASDPYSDFEKVTGRI DKNVSPEARHPLVAAFHYDRNNIAVGADESVVKEAH REVINSSTEGLLLNIDKDIRKILSGYIVEIEDTEGLKEVI NDRYDMLNISSLRQDGKTFIDFKKYNDKLPLYISNPN YKVNVYAVTKENTIINPSENGDTSTNGIKKILIFSKKG YEIG | 3 |
| | D2 + D4 | YPIVHVDMENIILSKNEDQSTQNTDSQTRTISKNTSTSR THTSEVHGNAEVHASFFDIGGSVSAGFSNSNSSTVAID | 4 |

TABLE 4-continued

| CAR portion | CAR of present invention | Amino acid or nucleic acid sequence | SEQ ID NO. |
|---|---|---|---|
| | | HSLSLAGERTWAETMGLNTADTARLNANIRYVNTGT APIYNVLPTTSLVLGKNQTLATIKAKENQLSQILAPNN YYPSKNLAPIALNAQDDFSSTPITMNYNQFLELEKTKQ LRLDTDQVYGNIATYNFENGRVRVDTGSNWSEVLPQI QETFHYDRNNIAVGADESVVKEAHREVINSSTEGLLL NIDKDIRKILSGYIVEIEDTEGLKEVINDRYDMLNISSL RQDGKTFIDFKKYNDKLPLYISNPNYKVNVYAVTKEN TIINPSENGDTSTNGIKKILIFSKKGYEIG | |
| | D3 + D4 | TARIIFNGKDLNLVERRIAAVNPSDPLETTKPDMTLKE ALKIAFGFNEPNGNLQYQGKDITEFDFNFDQQTSQNIK NQLAELNATNIYTVLDKIKLNAKMNILIRDKRFHYDR NNIAVGADESVVKEAHREVINSSTEGLLLNIDKDIRKI LSGYIVEIEDTEGLKEVINDRYDMLNISSLRQDGKTFID FKKYNDKLPLYISNPNYKVNVYAVTKENTIINPSENG DTSTNGIKKILIFSKKGYEIG | 5 |
| | D4 + D4 | FHYDRNNIAVGADESVVKEAHREVINSSTEGLLLNID KDIRKILSGYIVEIEDTEGLKEVINDRYDMLNISSLRQD GKTFIDFKKYNDKLPLYISNPNYKVNVYAVTKENTIIN PSENGDTSTNGIKKILIFSKKGYEIGFHYDRNNIAVGA DESVVKEAHREVINSSTEGLLLNIDKDIRKILSGYIVEIE DTEGLKEVINDRYDMLNISSLRQDGKTFIDFKKYNDK LPLYISNPNYKVNVYAVTKENTIINPSENGDTSTNGIK KILIFSKKGYEIG | 6 |
| | D1 + D2 + D4 | STSAGPTVPDRDNDGIPDSLEVEGYTVDVKNKRTFLSP WISNIHEKKGLTKYKSSPEKWSTASDPYSDFEKVTGRI DKNVSPEARHPLVAAYPIVHVDMENIILSKNEDQSTQ NTDSQTRTISKNTSTSRTHTSEVHGNAEVHASFFDIGG SVSAGFSNSNSSTVAIDHSLSLAGERTWAETMGLNTA DTARLNANIRYVNTGTAPIYNVLPTTSLVLGKNQTLA TIKAKENQLSQILAPNNYYPSKNLAPIALNAQDDFSST PITMNYNQFLELEKTKQLRLDTDQVYGNIATYNFENG RVRVDTGSNWSEVLPQIQETFHYDRNNIAVGADESVV KEAHREVINSSTEGLLLNIDKDIRKILSGYIVEIEDTEGL KEVINDRYDMLNISSLRQDGKTFIDFKKYNDKLPLYIS NPNYKVNVYAVTKENTIINPSENGDTSTNGIKKILIFSK KGYEIG | 7 |
| | D2 + D3 + D4 | YPIVHVDMENIILSKNEDQSTQNTDSQTRTISKNTSTSR THTSEVHGNAEVHASFFDIGGSVSAGFSNSNSSTVAID HSLSLAGERTWAETMGLNTADTARLNANIRYVNTGT APIYNVLPTTSLVLGKNQTLATIKAKENQLSQILAPNN YYPSKNLAPIALNAQDDFSSTPITMNYNQFLELEKTKQ LRLDTDQVYGNIATYNFENGRVRVDTGSNWSEVLPQI QETTARIIFNGKDLNLVERRIAAVNPSDPLETTKPDMT LKEALKIAFGFNEPNGNLQYQGKDITEFDFNFDQQTS QNIKNQLAELNATNIYTVLDKIKLNAKMNILIRDKRFH YDRNNIAVGADESVVKEAHREVINSSTEGLLLNIDKDI RKILSGYIVEIEDTEGLKEVINDRYDMLNISSLRQDGK TFIDFKKYNDKLPLYISNPNYKVNVYAVTKENTIINPS ENGDTSTNGIKKILIFSKKGYEIG | 8 |
| | D1 + D3 + D4 | STSAGPTVPDRDNDGIPDSLEVEGYTVDVKNKRTFLSP WISNIHEKKGLTKYKSSPEKWSTASDPYSDFEKVTGRI DKNVSPEARHPLVAATARIIFNGKDLNLVERRIAAVNP SDPLETTKPDMTLKEALKIAFGFNEPNGNLQYQGKDI TEFDFNFDQQTSQNIKNQLAELNATNIYTVLDKIKLNA KMNILIRDKRFHYDRNNIAVGADESVVKEAHREVINS STEGLLLNIDKDIRKILSGYIVEIEDTEGLKEVINDRYD MLNISSLRQDGKTFIDFKKYNDKLPLYISNPNYKVNV YAVTKENTIINPSENGDTSTNGIKKILIFSKKGYEIG | 9 |
| Trans-membrane domain | CD8 hinge and transmembrane domain | TTCGTGCCTGTGTTCCTGCCTGCCAAGCCTACCACA ACACCCGCTCCTAGACCTCCAACACCAGCTCCAACA ATCGCCAGCCAGCCTCTGTCTCTGAGGCCAGAAGCT TGTAGACCTGCTGCTGGCGGAGCCGTGCATACAAG AGGACTGGATTTCGCCTGCGACATCTACATCTGGGC CCCTCTGGCTGGAACATGTGGCGTTCTGCTGCTGAG CCTGGTCATCACCCTGTACTGCAACCACCGGAAC | 15 |
| Intracellular signaling domain | Primary CD3ζ signaling domain | AGAGTGAAGTTCAGCAGGAGCGCAGACGCCCCCGC GTACCAGCAGGGCCAGAACCAGCTCTATAACGAGC TCAATCTAGGACGAAGAGAGGAGTACGATGTTTTG GACAAGAGACGTGGCCGGGACCCTGAGATGGGGGG AAAGCCGAGAAGGAAGAACCCTCAGGAAGGCCTGT | 16 |

TABLE 4-continued

| CAR portion | CAR of present invention | | Amino acid or nucleic acid sequence | SEQ ID NO. |
|---|---|---|---|---|
| | | | ACAATGAACTGCAGAAAGATAAGATGGCGGAGGCC<br>TACAGTGAGATTGGGATGAAAGGCGAGCGCCGGAG<br>GGGCAAGGGGCACGATGGCCTTTACCAGGGTCTCA<br>GTACAGCCACCAAGGACACCTACGACGCCCTTCAC<br>ATGCAGGCCCTGCCCCCTCGC | |
| | Co-stimulatory signaling domain | CD28 | AGGAGTAAGAGGAGCAGGCTCCTGCACAGTGACTA<br>CATGAACATGACTCCCCGCCGCCCCGGGCCCACCC<br>GCAAGCATTACCAGCCCTATGCCCCACCACGCGACT<br>TCGCAGCCTATCGCTCC | 17 |
| | | CD137 | CGTTTCTCTGTTGTTAAACGGGGCAGAAAGAAGCTC<br>CTGTATATATTCAAACAACCATTTATGAGACCAGTA<br>CAAACTACTCAAGAGGAAGATGGCTGTAGCTGCCG<br>ATTTCCAGAAGAAGAAGAAGGAGGATGTGAACTG | 18 |
| Signal peptide | GM-CSF | | ATGTGGCTGCAGAGCCTGCTGCTCTTGGGCACTGTG<br>GCCTGCAGCATCTCT | 19 |

Nucleic acids encoding domain 1 to domain 4 of the PA63 ligand are shown in the following Table 5.

TABLE 5

| PA63 ligand domain | Nucleic acid sequence | SEQ ID NO. |
|---|---|---|
| D1 | AGTACAAGTGCTGGACCTACGGTTCCAGACCGTGACA<br>ATGATGGAATCCCTGATTCATTAGAGGTAGAAGGATA<br>TACGGTTGATGTCAAAAATAAAAGAACTTTTCTTTCA<br>CCATGGATTTCTAATATTCATGAAAAGAAAGGATTAA<br>CCAAATATAAATCATCTCCTGAAAAATGGAGCACGGC<br>TTCTGATCCGTACAGTGATTTCGAAAAGGTTACAGGA<br>CGGATTGATAAGAATGTATCACCAGAGGCAAGACAC<br>CCCCTTGTG | 20 |
| D2 | GCAGCTTATCCGATTGTACATGTAGATATGGAGAATA<br>TTATTCTCTCAAAAAATGAGGATCAATCCACACAGAA<br>TACTGATAGTCAAACGAGAACAATAAGTAAAAATAC<br>TTCTACAAGTAGGACACATACTAGTGAAGTACATGGA<br>AATGCAGAAGTGCATGCGTCGTTCTTTGATATTGGTG<br>GGAGTGTATCTGCAGGATTAGTAATTCGAATTCAAG<br>TACGGTCGCAATTGATCATTCACTATCTCTAGCAGGG<br>GAAAGAACTTGGGCTGAAACAATGGGTTTAAATACC<br>GCTGATACAGCAAGATTAAATGCCAATATTAGATATG<br>TAAATACTGGGACGGCTCCAATCTACAACGTGTTACC<br>AACGACTTCGTTAGTGTTAGGAAAAAATCAAACACTC<br>GCGACAATTAAAGCTAAGGAAAACCAATTAAGTCAA<br>ATACTTGCACCTAATAATTATTATCCTTCTAAAAACTT<br>GGCGCCAATCGCATTAAATGCACAAGACGATTTCAGT<br>TCTACTCCAATTACAATGAATTACAATCAATTTCTTGA<br>GTTAGAAAAAACGAAACAATTAAGATTAGATACGGA<br>TCAAGTATATGGGAATATAGCAACATACAATTTTGAA<br>AATGGAAGAGTGAGGGTGGATACAGGCTCGAACTGG<br>AGTGAAGTGTTACCGCAAATTCAAGAAACA | 21 |
| D3 | ACTGCACGTATCATTTTTAATGGAAAAGATTTAAATC<br>TGGTAGAAAGGCGGATAGCGGCGGTTAATCCTAGTG<br>ATCCATTAGAAACGACTAAACCGGATATGACATTAAA<br>AGAAGCCCTTAAAATAGCATTTGGATTTAACGAACCG<br>AATGGAAACTTACAATATCAAGGGAAAGACATAACC<br>GAATTTGATTTTAATTTCGATCAACAAACATCTCAAA<br>ATATCAAGAATCAGTTAGCGGAATTAAACGTAACTAA<br>CATATATACTGTATTAGATAAAATCAAATTAAATGCA<br>AAAATGAATATTTTAATAAGAGATAAACGT | 22 |
| D4 | TTTCATTATGATAGAAATAACATAGCAGTTGGGGCTG<br>ATGAGTCAGTAGTTAAGGAGGCTCATAGAGAAGTAA<br>TTAATTCGTCAACAGAGGGATTATTGTTAAATATTGA<br>TAAGGATATAAGAAAAATATTATCAGGTTATATTGTA<br>GAAATTGAAGATACTGAAGGGCTTAAAGAAGTTATA<br>AATGACAGATATGATATGTTGAATATTTCTAGTTTAC<br>GGCAAGATGGAAAAACATTTATAGATTTTAAAAAT<br>ATAATGATAAATTACCGTTATATATAAGTAATCCCAA |  23 |

TABLE 5-continued

| PA63 ligand domain | Nucleic acid sequence | SEQ ID NO. |
|---|---|---|
| | TTATAAGGTAAATGTATATGCTGTTACTAAAGAAAAC ACTATTATTAATCCTAGTGAGAATGGGGATACTAGTA CCAACGGGATCAAGAAAATTTTAATCTTTTCTAAAAA AGGCTATGAGATAGGA | |

The signal peptide, extracellular binding domain (D4, D1+D4, D2+D4, D3+D4, D4+D4, D1+D2+D4, D2+D3+D4 or D1+D3+D4), transmembrane domains (CD8 transmembrane & hinge) and intracellular signaling domains (CD3, CD134, CD28) of the CAR were amplified by PCR and were inserted into a TA cloning vector using DNA ligase.

The TA cloning vector was ligated and inserted into viral vectors (pMSCV, pCDH 521a) to express the fusion protein. A virus was produced using a lentiviral vector for introducing the CAR, and the lentiviral vector was induced in 293FT cells ($5\times10^6$), which are packaging cells, at an efficiency of about 90% or more. On the fourth day of induction of the lentivirus vector, a lentivirus was produced, the suspended cell medium was recovered and concentrated at 20,000 rpm using an ultra centrifuge for 2 hours, the concentrated lentivirus was transduced into 293FT cells, and the concentration was determined using a flow cytometer. The result showed that the lentivirus introduced with the CAR gene was obtained at a high yield of $3.4\times10^9$ IU/ml.

Example 3: Culture of CAR-T Cells

The lentivirus containing CAR introduced with the PA63 ligand, D4, D1+D4, D2+D4, D3+D4, D4+D4, D1+D2+D4, D2+D3+D4, or D1+D3+D4 produced in Example 2 was transduced at a concentration of 100 MOI into cytotoxic T-cell clones isolated from CTL (cytotoxic T lymphocytes) to produce CAR-T cells.

The expression was found to be induced at an efficiency of about 47.9% using flow cytometry, and only cells in which CAR expression was induced were selected using an Aria sorter. Rapid expansion protocol (REP) to amplify these cells in vitro was performed to increase the number of CAR cells, and pure CAR-T was observed to proliferate to a distribution of about 98% on the $10^{th}$ day of REP (FIG. 7).

The CTL used in this example was NYESO-1 CTL (MD Anderson Cancer Center (USA)). FIG. 8 shows conventional NYESO-1 CTL, which recognizes an NYESO-1 antigen and exhibits activity, and CAR-T cells, which are capable of simultaneously targeting NYESO-1 and ANTXR1 or ANTXR2, by introducing a CAR into the NYESO-1 CTL. The types of cancer cells on the left side of the drawing, targeted by NYESO-1 CTL, include malignant melanoma and synovial cell sarcoma. The NYESO-1 CTL is capable of inhibiting tumor progression or inducing tumor reduction.

In addition, CAR-T cells may be produced after inducing CAR using tumor-infiltrating lymphocytes (TILs) or T cells isolated from peripheral blood mononuclear cells (PBMCs).

Example 4: Confirmation of Anticancer Cytotoxicity of CAR-T Cells

Example 4-1: Confirmation of Cytotoxicity Against Pancreatic Cancer Cell Lines In order to confirm the anticancer cytotoxicity of the D4-containing CAR-introduced T cells produced in Example 3 against pancreatic cancer cell lines (PANC-1 and AsPC1), each of the pancreatic cancer cell lines was treated with the D4-containing CAR-introduced T cells.

Pancreatic cancer cell lines were seeded at $1\times10^5$ cells/well into a 96-well plate (round bottom), cultured with $1\times10^5$ cells/well of each of T cells not introduced with CAR, CAR-T containing D4, and CAR-T containing D4+D4 for 6 hours, and then treated with Golgi stop to inhibit the release of cytokine. After 6 hours, fixation and permeabilization were performed for intracellular staining, and the cells were stained using CD107a and IFN gamma antibodies. Then, CD107a, which is capable of indirectly detecting granule release, and IFN gamma, which is capable of detecting CAR-T cell activity, were identified using flow cytometry.

The result showed that T cells not introduced with CAR did not exhibit anticancer cytotoxicity or activity against pancreatic cancer cell lines, but that CAR-T cells exhibited anticancer cytotoxicity and activity against pancreatic cancer cell lines (FIG. 9). In FIG. 9, "T cell only" (negative control) is a T cell not introduced with CAR, and PMA/IONO (positive control) is treated with PMA/Ionomycin, which is a compound that functions to introduce extracellular ions (Ca', etc.) into cells, and may induce overactivity of the cells when treating T cells therewith. It can be used as an index to determine the extent of activity of T cells.

Thus, the effectiveness of the CAR-T cells containing the PA63 ligand could be detected as a therapeutic agent for the treatment of pancreatic cancer.

Example 4-2: Anticancer Cytotoxicity Against Melanoma Cell Lines and Pancreatic Cancer Cell Lines In order to confirm the anticancer cytotoxicity of the D4-containing CAR-introduced T cells and D4+D4-containing CAR-introduced T cells produced in Example 3, a pancreatic cancer cell line and a melanoma cell line were each treated with these cells.

The pancreatic cancer cell line and the melanoma cell line were each seeded at $1\times10^5$ cells/well into a 96-well plate (round bottom), cultured with $1\times10^5$ cells/well of wild-type cells (T cells not introduced with CAR), an empty vector control (T cells expressing vector including no D4 or D4+D4), D4-containing CAR-T, and D4+D4-containing CAR-T for 6 hours and then treated with Golgi stop to inhibit the release of cytokine. After 6 hours, fixation and permeabilization were performed for intracellular staining, and then the cells were stained using CD107a and IFN gamma antibodies. Then, CD107a, which is capable of indirectly detecting granule release, and IFN gamma, which is capable of detecting CAR-T cell activity, were identified using flow cytometry. The NYESO-1 CTL not introduced with CAR was used as a control.

The NYESO-1 CTL targets the melanoma cell line (526-mel) and thus exhibited anticancer cytotoxicity and activity against the melanoma cell line, regardless of the presence or absence of the CAR of the present invention (FIG. 10).

The result of detection of anticancer cytotoxicity against pancreatic cancer cell lines (AsPC1, PANC-1, Mia-PaCa2) showed that wild-type and empty vector control T cells did not exhibit anticancer cytotoxicity or activity against pancreatic cancer cell lines, but the D4-containing CAR-introduced T cells and the D4+D4 containing CAR-introduced T cells exhibited anticancer cytotoxicity and activity against pancreatic cancer cell lines (FIG. 10).

In addition, the lentivirus introduced with the CAR containing D4, D1+D4, D2+D4, D3+D4, or D1+D2+D3+D4 produced in Example 2 was transduced at a concentration of 100 of MOI into the NYESO-1 T-cell clone to produce CAR-T cells of each lentivirus.

$1\times10^6$ cells of PANC-1, a pancreatic cancer cell line, was collected in a 1.5 mL tube through centrifugation, released with 50 μL of FBS, mixed with 50 μL of $Cr^{51}$, and then stained in an incubator at 37° C. for 1 hour.

Then, the $Cr^{51}$-stained PANC-1 cell line was seeded at $1\times10^5$ cells/well in a 96-well plate (round bottom), and then were cultured with a vector control (T cells expressing a vector not containing D4 or each domain), CAR-T containing D4, and CAR-T containing D1+D4, D2+D4, D3+D4 or D1+D2+D3+D4 at a ratio of effector cells (CAR-T):target cells (PANC-1)=5($5\times10^5$): 1, 10($1\times10^6$):1, 20($2\times10^6$):1, or 40($4\times10^6$):1 for 4 hours, the medium in each well was then collected, and the release of $Cr^{51}$ was detected using a γ-counter. The result showed that all CAR-T excluding CAR-T containing D1+D4 exhibited excellent cytotoxicity, and among them, the CAR-T containing only D4 exhibited the most strongly cytotoxic effect (FIG. 11).

Example 5: Detection of Anticancer Cytotoxicity Against Pancreatic Cancer and Breast Cancer of CAR-T Cells Produced Using T Cells Isolated from PBMC The lentivirus introduced with the D4-containing CAR produced in Example 2 was transduced into PBMCs isolated from three healthy donors to produce CAR-T cells. In order to detect the anticancer cytotoxicity of D4-containing CAR-introduced T cells, each of melanoma, pancreatic cancer and breast cancer cell lines was treated with the CAR-T cells.

Melanoma, pancreatic cancer and breast cancer cell lines were seeded at $1\times10^5$ cells/well in a 96-well plate (round bottom), and were then cultured with $1\times10^5$ cells/well of NT (non-transduced) or CAR (D4-containing CAR-T) for 24 hours. In this case, treatment with Golgi stop was performed to inhibit the release of cytokine. After 24 hours, fixation and permeabilization were performed for intracellular staining, and then the cells were stained using IFN gamma antibody. Then, IFN gamma for detecting CAR-T cell activity was analyzed using flow cytometry. Melanoma (526-mel) and breast cancer cell lines (SK-BR3) that do not express ANTXR1 and ANTXR2 were used as controls.

Melanoma (526-mel) and breast cancer (SK-BR3) cell lines not expressing ANTXR1 and ANTXR2 were not targeted, and thus anticancer activity against 526-mel and SK-BR3 cell lines was not observed, regardless of the introduction of CAR according to this example (FIG. 12).

Meanwhile, anticancer cytotoxicity against pancreatic cancer cell lines (PANC-1, Mia-PaCa2) and breast cancer cell lines (MDA-231, ZR-571), reported to express ANTXR1 or ANTXR2, was observed. The result showed that NT (non-transduced) T cells did not exhibit anticancer cytotoxicity and activity, whereas D4-containing CAR-introduced T cells exhibited anticancer cytotoxicity and activity against pancreatic cancer and breast cancer cell lines (FIG. 12). Thus, CAR-T cells containing the PA63 ligand exhibited excellent toxicity against cancer cells expressing ANTXR1 or ANTXR2. Therefore, it is expected that the CAR-T cells will exhibit anticancer effects in all forms of cancer expressing ANTXR1 and ANTXR2.

Example 6: Detection of Cytotoxicity Against Pancreatic Cancer of CAR-T Cells Produced Using T Cells Isolated from PBMC A cell line (PANC-1 cell line expressing a red fluorescence protein (RFP); PANC-1_RFP) produced by introducing an RFP gene to exhibit fluorescence in the pancreatic cancer cell line, PANC-1, was seeded at $1\times10^4$ cells/well into each well of a 24-well plate and were then co-cultured with NT (non-transduced) T cells or CARs (D4-containing CAR-T) produced with PBMCs from healthy donors at a ratio of effector cells (CAR-T):target cells (PANC-1)=5($5\times10^4$):1, 10($1\times10^5$):1, 20($2\times10^5$):1, or 40($4\times10^5$):1 for 48 hours. The pancreatic cancer cell line (PANC-1_RFP) remaining in the 24-well plate was collected, and RFP-positive cells were counted using flow cytometry.

The result showed that cytotoxicity against the pancreatic cancer cell line (PANC-1_RFP) was detected at about 50% (5:1) to about 90% (40:1) (FIG. 13).

Example 7: Animal Model Using CAR-T Cells 25 days after subcutaneous injection of a pancreatic cancer cell line (Mia-PaCa2) in an amount of $1\times10^7$ cells/100 μL into immunodeficient mice (Balb/c Nude, female, 5 weeks old), PBS, NT (non-transduced) produced with PBMC from a healthy donor, GFP only (empty vector), and CAR (D4-containing CAR-T) were intravenously injected at a concentration of $1\times10^7$ cells/300 μL. About 4 weeks after cell injection, the D4-containing CAR-T exhibited a tumor volume decrease of about 80% compared to the controls (PBS, NT, and GFP only). This indicates that CAR-T exhibits excellent efficacy even in an animal model using solid cancer expressing ANTXR1 or ANTXR2 (FIG. 14).

6. INDUSTRIAL APPLICABILITY

Solid cancer can be treated using the anti-ANTXR chimeric antigen receptor (CAR)-T cells according to the present invention, and efficient and safe customized prevention or treatment of solid cancer is possible while restricting drug administration by administering chimeric antigen receptor (CAR)-T cells to solid cancer patients, particularly to pancreatic cancer patients for whom anticancer drugs are not effective.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

What is claimed is:

1. A nucleic acid encoding a chimeric antigen receptor (CAR) comprising an extracellular binding domain, a transmembrane domain, and an intracellular signaling domain, wherein the extracellular binding domain is domain 4 (D4) of a PA63 ligand or a fragment comprising domain 4 (D4) and domain 3 (D3) of a PA63 ligand, and recognizes an anthrax toxin receptor (ANTXR).

2. The nucleic acid according to claim 1, wherein the PA63 ligand comprises the amino acid sequence of SEQ ID NO:1.

3. The nucleic acid according to claim 1, wherein the domain 4 of the PA63 ligand comprises the amino acid sequence of SEQ ID NO:2.

4. The nucleic acid according to claim 1, wherein the fragment comprising domain 4 of the PA63 ligand comprises the amino acid sequence of SEQ ID NO: 5.

5. The nucleic acid according to claim 1, wherein the ANTXR is ARTXR1 (anthrax toxin receptor 1) or ARTXR2 (anthrax toxin receptor 2).

6. The nucleic acid according to claim 1, wherein the transmembrane domain is selected from the group consisting of an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, and CD154.

7. The nucleic acid according to claim 1, wherein the intracellular signaling domain comprises a primary signaling domain and a co-stimulatory signaling domain.

8. The nucleic acid according to claim 7, wherein the primary signaling domain is selected from the group consisting of TCRζ, FcRγ, FcRβ, CD3γ, CD3δ, CD3ε, CD3ζ, CD22, CD79a, CD79b, and CD66d.

9. The nucleic acid according to claim 7, wherein the co-stimulatory signaling domain is selected from the group consisting of OX40, CD2, CD27, CD28, CDS, ICAM-1, LFA-1 (CD11a/CD18), ICOS (CD278), and 4-1BB (CD137).

10. A vector comprising the nucleic acid encoding the chimeric antigen receptor according to claim 1.

11. The vector according to claim 10, wherein the vector is selected from the group consisting of DNA, RNA, plasmids, lentiviral vectors, adenovirus vectors, and retroviral vectors.

12. A recombinant cell comprising the vector according to claim 10.

13. The recombinant cell according to claim 12, wherein the cell is a T cell or NK cell.

14. The recombinant cell according to claim 13, wherein the T cell is selected from the group consisting of cytotoxic T lymphocytes (CTLs), tumor-infiltrating lymphocytes (TILs), and T cells isolated from peripheral blood mononuclear cells (PBMCs).

15. A method of inhibiting or delaying the progression of a solid cancer expressing an ANTXR (anthrax toxin receptor) or alleviating or eliminating symptoms of such solid cancer in a patient in need thereof, comprising administering to the patient a pharmaceutical composition comprising the recombinant cell according to claim 12.

16. The method according to claim 15, wherein the solid cancer is selected from the group consisting of pancreatic cancer, gastric cancer, colon cancer, lung cancer, breast cancer, germ cell cancer, liver cancer, skin cancer, bladder cancer, prostate cancer, uterine cancer, cervical cancer, and ovarian cancer.

* * * * *

UNITED STATES PATENT AND TRADEMARK OFFICE
CERTIFICATE OF CORRECTION

Page 1 of 1

PATENT NO. : 12,331,087 B2
APPLICATION NO. : 17/311619
DATED : June 17, 2025
INVENTOR(S) : Kyung-Mi Lee et al.

It is certified that error appears in the above-identified patent and that said Letters Patent is hereby corrected as shown below:

In the Specification

Column 3, Line 60, "CD8a, a CD32 chain" should be -- CD8α, a CD3ζ chain --.

Column 9, Line 8, "CD3" should be -- CD3ζ --.

Column 22, Line 30, "Ca'" should be -- $Ca^{2+}$ --.

Signed and Sealed this
Fourteenth Day of October, 2025

John A. Squires
*Director of the United States Patent and Trademark Office*

SEQUENCE LISTING

<160> NUMBER OF SEQ ID NOS: 27

<210> SEQ ID NO 1
<211> LENGTH: 568
<212> TYPE: PRT
<213> ORGANISM: Artificial Sequence
<220> FEATURE:
<223> OTHER INFORMATION: PA63 ligand

<400> SEQUENCE: 1

```
Ser Thr Ser Ala Gly Pro Thr Val Pro Asp Arg Asp Asn Asp Gly Ile
1               5                   10                  15

Pro Asp Ser Leu Glu Val Glu Gly Tyr Thr Val Asp Val Lys Asn Lys
                20                  25                  30

Arg Thr Phe Leu Ser Pro Trp Ile Ser Asn Ile His Glu Lys Lys Gly
            35                  40                  45

Leu Thr Lys Tyr Lys Ser Ser Pro Glu Lys Trp Ser Thr Ala Ser Asp
        50                  55                  60

Pro Tyr Ser Asp Phe Glu Lys Val Thr Gly Arg Ile Asp Lys Asn Val
65                  70                  75                  80

Ser Pro Glu Ala Arg His Pro Leu Val Ala Ala Tyr Pro Ile Val His
                85                  90                  95

Val Asp Met Glu Asn Ile Ile Leu Ser Lys Asn Glu Asp Gln Ser Thr
                100                 105                 110

Gln Asn Thr Asp Ser Gln Thr Arg Thr Ile Ser Lys Asn Thr Ser Thr
            115                 120                 125

Ser Arg Thr His Thr Ser Glu Val His Gly Asn Ala Glu Val His Ala
        130                 135                 140

Ser Phe Phe Asp Ile Gly Gly Ser Val Ser Ala Gly Phe Ser Asn Ser
145                 150                 155                 160

Asn Ser Ser Thr Val Ala Ile Asp His Ser Leu Ser Leu Ala Gly Glu
                165                 170                 175

Arg Thr Trp Ala Glu Thr Met Gly Leu Asn Thr Ala Asp Thr Ala Arg
            180                 185                 190

Leu Asn Ala Asn Ile Arg Tyr Val Asn Thr Gly Thr Ala Pro Ile Tyr
        195                 200                 205

Asn Val Leu Pro Thr Thr Ser Leu Val Leu Gly Lys Asn Gln Thr Leu
    210                 215                 220

Ala Thr Ile Lys Ala Lys Glu Asn Gln Leu Ser Gln Ile Leu Ala Pro
225                 230                 235                 240

Asn Asn Tyr Tyr Pro Ser Lys Asn Leu Ala Pro Ile Ala Leu Asn Ala
                245                 250                 255

Gln Asp Asp Phe Ser Ser Thr Pro Ile Thr Met Asn Tyr Asn Gln Phe
            260                 265                 270

Leu Glu Leu Glu Lys Thr Lys Gln Leu Arg Leu Asp Thr Asp Gln Val
        275                 280                 285

Tyr Gly Asn Ile Ala Thr Tyr Asn Phe Glu Asn Gly Arg Val Arg Val
    290                 295                 300

Asp Thr Gly Ser Asn Trp Ser Glu Val Leu Pro Gln Ile Gln Glu Thr
305                 310                 315                 320

Thr Ala Arg Ile Ile Phe Asn Gly Lys Asp Leu Asn Leu Val Glu Arg
                325                 330                 335

Arg Ile Ala Ala Val Asn Pro Ser Asp Pro Leu Glu Thr Thr Lys Pro
            340                 345                 350

Asp Met Thr Leu Lys Glu Ala Leu Lys Ile Ala Phe Gly Phe Asn Glu
```

```
                355                 360                 365
Pro Asn Gly Asn Leu Gln Tyr Gln Gly Lys Asp Ile Thr Glu Phe Asp
    370                 375                 380

Phe Asn Phe Asp Gln Gln Thr Ser Gln Asn Ile Lys Asn Gln Leu Ala
385                 390                 395                 400

Glu Leu Asn Ala Thr Asn Ile Tyr Thr Val Leu Asp Lys Ile Lys Leu
                405                 410                 415

Asn Ala Lys Met Asn Ile Leu Ile Arg Asp Lys Arg Phe His Tyr Asp
            420                 425                 430

Arg Asn Asn Ile Ala Val Gly Ala Asp Glu Ser Val Val Lys Glu Ala
        435                 440                 445

His Arg Glu Val Ile Asn Ser Ser Thr Glu Gly Leu Leu Leu Asn Ile
    450                 455                 460

Asp Lys Asp Ile Arg Lys Ile Leu Ser Gly Tyr Ile Val Glu Ile Glu
465                 470                 475                 480

Asp Thr Glu Gly Leu Lys Glu Val Ile Asn Asp Arg Tyr Asp Met Leu
                485                 490                 495

Asn Ile Ser Ser Leu Arg Gln Asp Gly Lys Thr Phe Ile Asp Phe Lys
            500                 505                 510

Lys Tyr Asn Asp Lys Leu Pro Leu Tyr Ile Ser Asn Pro Asn Tyr Lys
        515                 520                 525

Val Asn Val Tyr Ala Val Thr Lys Glu Asn Thr Ile Ile Asn Pro Ser
    530                 535                 540

Glu Asn Gly Asp Thr Ser Thr Asn Gly Ile Lys Lys Ile Leu Ile Phe
545                 550                 555                 560

Ser Lys Lys Gly Tyr Glu Ile Gly
                565

<210> SEQ ID NO 2
<211> LENGTH: 140
<212> TYPE: PRT
<213> ORGANISM: Artificial Sequence
<220> FEATURE:
<223> OTHER INFORMATION: D4

<400> SEQUENCE: 2

Phe His Tyr Asp Arg Asn Asn Ile Ala Val Gly Ala Asp Glu Ser Val
1               5                   10                  15

Val Lys Glu Ala His Arg Glu Val Ile Asn Ser Ser Thr Glu Gly Leu
            20                  25                  30

Leu Leu Asn Ile Asp Lys Asp Ile Arg Lys Ile Leu Ser Gly Tyr Ile
        35                  40                  45

Val Glu Ile Glu Asp Thr Glu Gly Leu Lys Glu Val Ile Asn Asp Arg
    50                  55                  60

Tyr Asp Met Leu Asn Ile Ser Ser Leu Arg Gln Asp Gly Lys Thr Phe
65                  70                  75                  80

Ile Asp Phe Lys Lys Tyr Asn Asp Lys Leu Pro Leu Tyr Ile Ser Asn
                85                  90                  95

Pro Asn Tyr Lys Val Asn Val Tyr Ala Val Thr Lys Glu Asn Thr Ile
            100                 105                 110

Ile Asn Pro Ser Glu Asn Gly Asp Thr Ser Thr Asn Gly Ile Lys Lys
        115                 120                 125

Ile Leu Ile Phe Ser Lys Lys Gly Tyr Glu Ile Gly
    130                 135                 140
```

```
<210> SEQ ID NO 3
<211> LENGTH: 231
<212> TYPE: PRT
<213> ORGANISM: Artificial Sequence
<220> FEATURE:
<223> OTHER INFORMATION: D1 + D4

<400> SEQUENCE: 3

Ser Thr Ser Ala Gly Pro Thr Val Pro Asp Arg Asp Asn Asp Gly Ile
1               5                   10                  15

Pro Asp Ser Leu Glu Val Glu Gly Tyr Thr Val Asp Val Lys Asn Lys
            20                  25                  30

Arg Thr Phe Leu Ser Pro Trp Ile Ser Asn Ile His Glu Lys Lys Gly
        35                  40                  45

Leu Thr Lys Tyr Lys Ser Ser Pro Glu Lys Trp Ser Thr Ala Ser Asp
    50                  55                  60

Pro Tyr Ser Asp Phe Glu Lys Val Thr Gly Arg Ile Asp Lys Asn Val
65                  70                  75                  80

Ser Pro Glu Ala Arg His Pro Leu Val Ala Ala Phe His Tyr Asp Arg
                85                  90                  95

Asn Asn Ile Ala Val Gly Ala Asp Glu Ser Val Val Lys Glu Ala His
            100                 105                 110

Arg Glu Val Ile Asn Ser Ser Thr Glu Gly Leu Leu Leu Asn Ile Asp
        115                 120                 125

Lys Asp Ile Arg Lys Ile Leu Ser Gly Tyr Ile Val Glu Ile Glu Asp
    130                 135                 140

Thr Glu Gly Leu Lys Glu Val Ile Asn Asp Arg Tyr Asp Met Leu Asn
145                 150                 155                 160

Ile Ser Ser Leu Arg Gln Asp Gly Lys Thr Phe Ile Asp Phe Lys Lys
                165                 170                 175

Tyr Asn Asp Lys Leu Pro Leu Tyr Ile Ser Asn Pro Asn Tyr Lys Val
            180                 185                 190

Asn Val Tyr Ala Val Thr Lys Glu Asn Thr Ile Ile Asn Pro Ser Glu
        195                 200                 205

Asn Gly Asp Thr Ser Thr Asn Gly Ile Lys Lys Ile Leu Ile Phe Ser
    210                 215                 220

Lys Lys Gly Tyr Glu Ile Gly
225                 230

<210> SEQ ID NO 4
<211> LENGTH: 369
<212> TYPE: PRT
<213> ORGANISM: Artificial Sequence
<220> FEATURE:
<223> OTHER INFORMATION: D2 + D4

<400> SEQUENCE: 4

Tyr Pro Ile Val His Val Asp Met Glu Asn Ile Ile Leu Ser Lys Asn
1               5                   10                  15

Glu Asp Gln Ser Thr Gln Asn Thr Asp Ser Gln Thr Arg Thr Ile Ser
            20                  25                  30

Lys Asn Thr Ser Thr Ser Arg Thr His Thr Ser Glu Val His Gly Asn
        35                  40                  45

Ala Glu Val His Ala Ser Phe Phe Asp Ile Gly Gly Ser Val Ser Ala
    50                  55                  60

Gly Phe Ser Asn Ser Asn Ser Ser Thr Val Ala Ile Asp His Ser Leu
65                  70                  75                  80
```

```
Ser Leu Ala Gly Glu Arg Thr Trp Ala Glu Thr Met Gly Leu Asn Thr
                85                  90                  95

Ala Asp Thr Ala Arg Leu Asn Ala Asn Ile Arg Tyr Val Asn Thr Gly
            100                 105                 110

Thr Ala Pro Ile Tyr Asn Val Leu Pro Thr Thr Ser Leu Val Leu Gly
            115                 120                 125

Lys Asn Gln Thr Leu Ala Thr Ile Lys Ala Lys Glu Asn Gln Leu Ser
            130                 135                 140

Gln Ile Leu Ala Pro Asn Asn Tyr Tyr Pro Ser Lys Asn Leu Ala Pro
145                 150                 155                 160

Ile Ala Leu Asn Ala Gln Asp Asp Phe Ser Ser Thr Pro Ile Thr Met
                165                 170                 175

Asn Tyr Asn Gln Phe Leu Glu Leu Glu Lys Thr Lys Gln Leu Arg Leu
            180                 185                 190

Asp Thr Asp Gln Val Tyr Gly Asn Ile Ala Thr Tyr Asn Phe Glu Asn
            195                 200                 205

Gly Arg Val Arg Val Asp Thr Gly Ser Asn Trp Ser Glu Val Leu Pro
            210                 215                 220

Gln Ile Gln Glu Thr Phe His Tyr Asp Arg Asn Asn Ile Ala Val Gly
225                 230                 235                 240

Ala Asp Glu Ser Val Val Lys Glu Ala His Arg Glu Val Ile Asn Ser
                245                 250                 255

Ser Thr Glu Gly Leu Leu Leu Asn Ile Asp Lys Asp Ile Arg Lys Ile
            260                 265                 270

Leu Ser Gly Tyr Ile Val Glu Ile Glu Asp Thr Glu Gly Leu Lys Glu
            275                 280                 285

Val Ile Asn Asp Arg Tyr Asp Met Leu Asn Ile Ser Ser Leu Arg Gln
290                 295                 300

Asp Gly Lys Thr Phe Ile Asp Phe Lys Lys Tyr Asn Asp Lys Leu Pro
305                 310                 315                 320

Leu Tyr Ile Ser Asn Pro Asn Tyr Lys Val Asn Val Tyr Ala Val Thr
                325                 330                 335

Lys Glu Asn Thr Ile Ile Asn Pro Ser Glu Asn Gly Asp Thr Ser Thr
            340                 345                 350

Asn Gly Ile Lys Lys Ile Leu Ile Phe Ser Lys Lys Gly Tyr Glu Ile
            355                 360                 365

Gly
```

<210> SEQ ID NO 5
<211> LENGTH: 248
<212> TYPE: PRT
<213> ORGANISM: Artificial Sequence
<220> FEATURE:
<223> OTHER INFORMATION: D3 + D4

<400> SEQUENCE: 5

```
Thr Ala Arg Ile Ile Phe Asn Gly Lys Asp Leu Asn Leu Val Glu Arg
1               5                   10                  15

Arg Ile Ala Ala Val Asn Pro Ser Asp Pro Leu Glu Thr Thr Lys Pro
            20                  25                  30

Asp Met Thr Leu Lys Glu Ala Leu Lys Ile Ala Phe Gly Phe Asn Glu
            35                  40                  45

Pro Asn Gly Asn Leu Gln Tyr Gln Gly Lys Asp Ile Thr Glu Phe Asp
            50                  55                  60

Phe Asn Phe Asp Gln Gln Thr Ser Gln Asn Ile Lys Asn Gln Leu Ala
```

```
                65                  70                  75                  80
Glu Leu Asn Ala Thr Asn Ile Tyr Thr Val Leu Asp Lys Ile Lys Leu
                    85                  90                  95

Asn Ala Lys Met Asn Ile Leu Ile Arg Asp Lys Arg Phe His Tyr Asp
                100                 105                 110

Arg Asn Asn Ile Ala Val Gly Ala Asp Glu Ser Val Lys Glu Ala
                115                 120                 125

His Arg Glu Val Ile Asn Ser Ser Thr Glu Gly Leu Leu Asn Ile
            130                 135                 140

Asp Lys Asp Ile Arg Lys Ile Leu Ser Gly Tyr Ile Val Glu Ile Glu
145                 150                 155                 160

Asp Thr Glu Gly Leu Lys Glu Val Ile Asn Asp Arg Tyr Asp Met Leu
                165                 170                 175

Asn Ile Ser Ser Leu Arg Gln Asp Gly Lys Thr Phe Ile Asp Phe Lys
                180                 185                 190

Lys Tyr Asn Asp Lys Leu Pro Leu Tyr Ile Ser Asn Pro Asn Tyr Lys
                195                 200                 205

Val Asn Val Tyr Ala Val Thr Lys Glu Asn Thr Ile Ile Asn Pro Ser
            210                 215                 220

Glu Asn Gly Asp Thr Ser Thr Asn Gly Ile Lys Lys Ile Leu Ile Phe
225                 230                 235                 240

Ser Lys Lys Gly Tyr Glu Ile Gly
                245

<210> SEQ ID NO 6
<211> LENGTH: 280
<212> TYPE: PRT
<213> ORGANISM: Artificial Sequence
<220> FEATURE:
<223> OTHER INFORMATION: D4 + D4

<400> SEQUENCE: 6

Phe His Tyr Asp Arg Asn Asn Ile Ala Val Gly Ala Asp Glu Ser Val
1               5                   10                  15

Val Lys Glu Ala His Arg Glu Val Ile Asn Ser Ser Thr Glu Gly Leu
                20                  25                  30

Leu Leu Asn Ile Asp Lys Asp Ile Arg Lys Ile Leu Ser Gly Tyr Ile
                35                  40                  45

Val Glu Ile Glu Asp Thr Glu Gly Leu Lys Glu Val Ile Asn Asp Arg
            50                  55                  60

Tyr Asp Met Leu Asn Ile Ser Ser Leu Arg Gln Asp Gly Lys Thr Phe
65              70                  75                  80

Ile Asp Phe Lys Lys Tyr Asn Asp Lys Leu Pro Leu Tyr Ile Ser Asn
                85                  90                  95

Pro Asn Tyr Lys Val Asn Val Tyr Ala Val Thr Lys Glu Asn Thr Ile
                100                 105                 110

Ile Asn Pro Ser Glu Asn Gly Asp Thr Ser Thr Asn Gly Ile Lys Lys
                115                 120                 125

Ile Leu Ile Phe Ser Lys Lys Gly Tyr Glu Ile Gly Phe His Tyr Asp
            130                 135                 140

Arg Asn Asn Ile Ala Val Gly Ala Asp Glu Ser Val Val Lys Glu Ala
145                 150                 155                 160

His Arg Glu Val Ile Asn Ser Ser Thr Glu Gly Leu Leu Leu Asn Ile
                165                 170                 175

Asp Lys Asp Ile Arg Lys Ile Leu Ser Gly Tyr Ile Val Glu Ile Glu
```

```
                    180                 185                 190
Asp Thr Glu Gly Leu Lys Glu Val Ile Asn Asp Arg Tyr Asp Met Leu
                195                 200                 205

Asn Ile Ser Ser Leu Arg Gln Asp Gly Lys Thr Phe Ile Asp Phe Lys
            210                 215                 220

Lys Tyr Asn Asp Lys Leu Pro Leu Tyr Ile Ser Asn Pro Asn Tyr Lys
225                 230                 235                 240

Val Asn Val Tyr Ala Val Thr Lys Glu Asn Thr Ile Ile Asn Pro Ser
                245                 250                 255

Glu Asn Gly Asp Thr Ser Thr Asn Gly Ile Lys Lys Ile Leu Ile Phe
            260                 265                 270

Ser Lys Lys Gly Tyr Glu Ile Gly
            275                 280

<210> SEQ ID NO 7
<211> LENGTH: 460
<212> TYPE: PRT
<213> ORGANISM: Artificial Sequence
<220> FEATURE:
<223> OTHER INFORMATION: D1 + D2 + D4

<400> SEQUENCE: 7

Ser Thr Ser Ala Gly Pro Thr Val Pro Asp Arg Asp Asn Asp Gly Ile
1               5                   10                  15

Pro Asp Ser Leu Glu Val Glu Gly Tyr Thr Val Asp Val Lys Asn Lys
                20                  25                  30

Arg Thr Phe Leu Ser Pro Trp Ile Ser Asn Ile His Glu Lys Lys Gly
            35                  40                  45

Leu Thr Lys Tyr Lys Ser Ser Pro Glu Lys Trp Ser Thr Ala Ser Asp
        50                  55                  60

Pro Tyr Ser Asp Phe Glu Lys Val Thr Gly Arg Ile Asp Lys Asn Val
65                  70                  75                  80

Ser Pro Glu Ala Arg His Pro Leu Val Ala Ala Tyr Pro Ile Val His
                85                  90                  95

Val Asp Met Glu Asn Ile Ile Leu Ser Lys Asn Glu Asp Gln Ser Thr
                100                 105                 110

Gln Asn Thr Asp Ser Gln Thr Arg Thr Ile Ser Lys Asn Thr Ser Thr
            115                 120                 125

Ser Arg Thr His Thr Ser Glu Val His Gly Asn Ala Glu Val His Ala
        130                 135                 140

Ser Phe Phe Asp Ile Gly Gly Ser Val Ser Ala Gly Phe Ser Asn Ser
145                 150                 155                 160

Asn Ser Ser Thr Val Ala Ile Asp His Ser Leu Ser Leu Ala Gly Glu
                165                 170                 175

Arg Thr Trp Ala Glu Thr Met Gly Leu Asn Thr Ala Asp Thr Ala Arg
            180                 185                 190

Leu Asn Ala Asn Ile Arg Tyr Val Asn Thr Gly Thr Ala Pro Ile Tyr
        195                 200                 205

Asn Val Leu Pro Thr Thr Ser Leu Val Leu Gly Lys Asn Gln Thr Leu
    210                 215                 220

Ala Thr Ile Lys Ala Lys Glu Asn Gln Leu Ser Gln Ile Leu Ala Pro
225                 230                 235                 240

Asn Asn Tyr Tyr Pro Ser Lys Asn Leu Ala Pro Ile Ala Leu Asn Ala
                245                 250                 255

Gln Asp Asp Phe Ser Ser Thr Pro Ile Thr Met Asn Tyr Asn Gln Phe
```

```
                    260                 265                 270
Leu Glu Leu Glu Lys Thr Lys Gln Leu Arg Leu Asp Thr Asp Gln Val
        275                 280                 285

Tyr Gly Asn Ile Ala Thr Tyr Asn Phe Glu Asn Gly Arg Val Arg Val
        290                 295                 300

Asp Thr Gly Ser Asn Trp Ser Glu Val Leu Pro Gln Ile Gln Glu Thr
305                 310                 315                 320

Phe His Tyr Asp Arg Asn Asn Ile Ala Val Gly Ala Asp Glu Ser Val
                325                 330                 335

Val Lys Glu Ala His Arg Glu Val Ile Asn Ser Ser Thr Glu Gly Leu
        340                 345                 350

Leu Leu Asn Ile Asp Lys Asp Ile Arg Lys Ile Leu Ser Gly Tyr Ile
        355                 360                 365

Val Glu Ile Glu Asp Thr Glu Gly Leu Lys Glu Val Ile Asn Asp Arg
        370                 375                 380

Tyr Asp Met Leu Asn Ile Ser Ser Leu Arg Gln Asp Gly Lys Thr Phe
385                 390                 395                 400

Ile Asp Phe Lys Lys Tyr Asn Asp Lys Leu Pro Leu Tyr Ile Ser Asn
                405                 410                 415

Pro Asn Tyr Lys Val Asn Val Tyr Ala Val Thr Lys Glu Asn Thr Ile
                420                 425                 430

Ile Asn Pro Ser Glu Asn Gly Asp Thr Ser Thr Asn Gly Ile Lys Lys
        435                 440                 445

Ile Leu Ile Phe Ser Lys Lys Gly Tyr Glu Ile Gly
        450                 455                 460

<210> SEQ ID NO 8
<211> LENGTH: 477
<212> TYPE: PRT
<213> ORGANISM: Artificial Sequence
<220> FEATURE:
<223> OTHER INFORMATION: D2 + D3 + D4

<400> SEQUENCE: 8

Tyr Pro Ile Val His Val Asp Met Glu Asn Ile Ile Leu Ser Lys Asn
1               5                   10                  15

Glu Asp Gln Ser Thr Gln Asn Thr Asp Ser Gln Thr Arg Thr Ile Ser
                20                  25                  30

Lys Asn Thr Ser Thr Ser Arg Thr His Thr Ser Glu Val His Gly Asn
        35                  40                  45

Ala Glu Val His Ala Ser Phe Phe Asp Ile Gly Gly Ser Val Ser Ala
    50                  55                  60

Gly Phe Ser Asn Ser Asn Ser Ser Thr Val Ala Ile Asp His Ser Leu
65                  70                  75                  80

Ser Leu Ala Gly Glu Arg Thr Trp Ala Glu Thr Met Gly Leu Asn Thr
                85                  90                  95

Ala Asp Thr Ala Arg Leu Asn Ala Asn Ile Arg Tyr Val Asn Thr Gly
                100                 105                 110

Thr Ala Pro Ile Tyr Asn Val Leu Pro Thr Thr Ser Leu Val Leu Gly
            115                 120                 125

Lys Asn Gln Thr Leu Ala Thr Ile Lys Ala Lys Glu Asn Gln Leu Ser
        130                 135                 140

Gln Ile Leu Ala Pro Asn Asn Tyr Tyr Pro Ser Lys Asn Leu Ala Pro
145                 150                 155                 160

Ile Ala Leu Asn Ala Gln Asp Asp Phe Ser Ser Thr Pro Ile Thr Met
```

```
                    165                 170                 175
Asn Tyr Asn Gln Phe Leu Glu Leu Glu Lys Thr Lys Gln Leu Arg Leu
                180                 185                 190

Asp Thr Asp Gln Val Tyr Gly Asn Ile Ala Thr Tyr Asn Phe Glu Asn
            195                 200                 205

Gly Arg Val Arg Val Asp Thr Gly Ser Asn Trp Ser Glu Val Leu Pro
        210                 215                 220

Gln Ile Gln Glu Thr Thr Ala Arg Ile Ile Phe Asn Gly Lys Asp Leu
225                 230                 235                 240

Asn Leu Val Glu Arg Arg Ile Ala Ala Val Asn Pro Ser Asp Pro Leu
                245                 250                 255

Glu Thr Thr Lys Pro Asp Met Thr Leu Lys Glu Ala Leu Lys Ile Ala
            260                 265                 270

Phe Gly Phe Asn Glu Pro Asn Gly Asn Leu Gln Tyr Gln Gly Lys Asp
        275                 280                 285

Ile Thr Glu Phe Asp Phe Asn Phe Asp Gln Gln Thr Ser Gln Asn Ile
290                 295                 300

Lys Asn Gln Leu Ala Glu Leu Asn Ala Thr Asn Ile Tyr Thr Val Leu
305                 310                 315                 320

Asp Lys Ile Lys Leu Asn Ala Lys Met Asn Ile Leu Ile Arg Asp Lys
                325                 330                 335

Arg Phe His Tyr Asp Arg Asn Asn Ile Ala Val Gly Ala Asp Glu Ser
            340                 345                 350

Val Val Lys Glu Ala His Arg Glu Val Ile Asn Ser Ser Thr Glu Gly
        355                 360                 365

Leu Leu Leu Asn Ile Asp Lys Asp Ile Arg Lys Ile Leu Ser Gly Tyr
        370                 375                 380

Ile Val Glu Ile Glu Asp Thr Glu Gly Leu Lys Glu Val Ile Asn Asp
385                 390                 395                 400

Arg Tyr Asp Met Leu Asn Ile Ser Ser Leu Arg Gln Asp Gly Lys Thr
                405                 410                 415

Phe Ile Asp Phe Lys Lys Tyr Asn Asp Lys Leu Pro Leu Tyr Ile Ser
            420                 425                 430

Asn Pro Asn Tyr Lys Val Asn Val Tyr Ala Val Thr Lys Glu Asn Thr
        435                 440                 445

Ile Ile Asn Pro Ser Glu Asn Gly Asp Thr Ser Thr Asn Gly Ile Lys
    450                 455                 460

Lys Ile Leu Ile Phe Ser Lys Lys Gly Tyr Glu Ile Gly
465                 470                 475

<210> SEQ ID NO 9
<211> LENGTH: 339
<212> TYPE: PRT
<213> ORGANISM: Artificial Sequence
<220> FEATURE:
<223> OTHER INFORMATION: D1 + D3 + D4

<400> SEQUENCE: 9

Ser Thr Ser Ala Gly Pro Thr Val Pro Asp Arg Asp Asn Asp Gly Ile
1               5                   10                  15

Pro Asp Ser Leu Glu Val Glu Gly Tyr Thr Val Asp Val Lys Asn Lys
                20                  25                  30

Arg Thr Phe Leu Ser Pro Trp Ile Ser Asn Ile His Glu Lys Lys Gly
            35                  40                  45

Leu Thr Lys Tyr Lys Ser Ser Pro Glu Lys Trp Ser Thr Ala Ser Asp
```

50                  55                  60
Pro Tyr Ser Asp Phe Glu Lys Val Thr Gly Arg Ile Asp Lys Asn Val
 65                  70                  75                  80

Ser Pro Glu Ala Arg His Pro Leu Val Ala Thr Ala Arg Ile Ile
                 85                  90                  95

Phe Asn Gly Lys Asp Leu Asn Leu Val Glu Arg Arg Ile Ala Ala Val
                100                 105                 110

Asn Pro Ser Asp Pro Leu Glu Thr Thr Lys Pro Asp Met Thr Leu Lys
            115                 120                 125

Glu Ala Leu Lys Ile Ala Phe Gly Phe Asn Glu Pro Asn Gly Asn Leu
        130                 135                 140

Gln Tyr Gln Gly Lys Asp Ile Thr Glu Phe Asp Phe Asn Phe Asp Gln
145                 150                 155                 160

Gln Thr Ser Gln Asn Ile Lys Asn Gln Leu Ala Glu Leu Asn Ala Thr
                165                 170                 175

Asn Ile Tyr Thr Val Leu Asp Lys Ile Lys Leu Asn Ala Lys Met Asn
            180                 185                 190

Ile Leu Ile Arg Asp Lys Arg Phe His Tyr Asp Arg Asn Asn Ile Ala
        195                 200                 205

Val Gly Ala Asp Glu Ser Val Val Lys Glu Ala His Arg Glu Val Ile
    210                 215                 220

Asn Ser Ser Thr Glu Gly Leu Leu Leu Asn Ile Asp Lys Asp Ile Arg
225                 230                 235                 240

Lys Ile Leu Ser Gly Tyr Ile Val Glu Ile Glu Asp Thr Glu Gly Leu
                245                 250                 255

Lys Glu Val Ile Asn Asp Arg Tyr Asp Met Leu Asn Ile Ser Ser Leu
            260                 265                 270

Arg Gln Asp Gly Lys Thr Phe Ile Asp Phe Lys Lys Tyr Asn Asp Lys
        275                 280                 285

Leu Pro Leu Tyr Ile Ser Asn Pro Asn Tyr Lys Val Asn Val Tyr Ala
    290                 295                 300

Val Thr Lys Glu Asn Thr Ile Ile Asn Pro Ser Glu Asn Gly Asp Thr
305                 310                 315                 320

Ser Thr Asn Gly Ile Lys Lys Ile Leu Ile Phe Ser Lys Lys Gly Tyr
                325                 330                 335

Glu Ile Gly

<210> SEQ ID NO 10
<211> LENGTH: 25
<212> TYPE: PRT
<213> ORGANISM: Artificial Sequence
<220> FEATURE:
<223> OTHER INFORMATION: Linker

<400> SEQUENCE: 10

Gly Gly Gly Gly Ser Gly Gly Gly Ser Gly Gly Gly Ser Gly
 1               5                  10                  15

Gly Gly Gly Ser Gly Gly Gly Gly Ser
            20                  25

<210> SEQ ID NO 11
<211> LENGTH: 198
<212> TYPE: DNA
<213> ORGANISM: Artificial Sequence
<220> FEATURE:
<223> OTHER INFORMATION: Transmembrane domain

<400> SEQUENCE: 11

| | |
|---|---:|
| accacgacgc cagcgccgcg accaccaaca ccggcgccca ccatcgcgtc gcagcccctg | 60 |
| tccctgcgcc cagaggcgtg ccggccagcg gcggggggcg cagtgcacac gagggggctg | 120 |
| gacttcgcct gtgatatcta catctgggcg cccttggccg ggacttgtgg ggtccttctc | 180 |
| ctgtcactgg ttatcacc | 198 |

<210> SEQ ID NO 12
<211> LENGTH: 341
<212> TYPE: DNA
<213> ORGANISM: Artificial Sequence
<220> FEATURE:
<223> OTHER INFORMATION: Primary signaling domain

<400> SEQUENCE: 12

| | |
|---|---:|
| ctgagagtga agttcagcag gagcgcagac gcccccgcgt accagcaggg ccagaaccag | 60 |
| ctctataacg agctcaatct aggacgaaga gaggagtacg atgttttgga caagagacgt | 120 |
| ggccgggacc ctgagatggg gggaaagccg agaaggaaga ccctcagga aggcctgtac | 180 |
| aatgaactgc agaaagataa gatggcggag gcctacagtg agattgggat gaaaggcgag | 240 |
| cgccggaggg gcaaggggca cgatggcctt taccagggtc tcagtacagc caccaaggac | 300 |
| acctacgacg cccttcacat gcaggccctg ccccctcgct a | 341 |

<210> SEQ ID NO 13
<211> LENGTH: 204
<212> TYPE: DNA
<213> ORGANISM: Artificial Sequence
<220> FEATURE:
<223> OTHER INFORMATION: Co-stimulatory signaling domain

<400> SEQUENCE: 13

| | |
|---|---:|
| ttttgggtgc tggtggtggt tggtggagtc ctggcttgct atagcttgct agtaacagtg | 60 |
| gcctttatta ttttctgggt gaggagtaag aggagcaggc tcctgcacag tgactacatg | 120 |
| aacatgactc cccgccgccc cgggcccacc cgcaagcatt accagcccta tgccccacca | 180 |
| cgcgacttcg cagcctatcg ctcc | 204 |

<210> SEQ ID NO 14
<211> LENGTH: 126
<212> TYPE: DNA
<213> ORGANISM: Artificial Sequence
<220> FEATURE:
<223> OTHER INFORMATION: Co-stimulatory signaling domain

<400> SEQUENCE: 14

| | |
|---|---:|
| aaacggggca gaaagaaact cctgtatata ttcaaacaac catttatgag accagtacaa | 60 |
| actactcaag aggaagatgg ctgtagctgc cgatttccag aagaagaaga aggaggatgt | 120 |
| gaactg | 126 |

<210> SEQ ID NO 15
<211> LENGTH: 249
<212> TYPE: DNA
<213> ORGANISM: Artificial Sequence
<220> FEATURE:
<223> OTHER INFORMATION: Transmembrane domain

<400> SEQUENCE: 15

| | |
|---|---:|
| ttcgtgcctg tgttcctgcc tgccaagcct accacaacac ccgctcctag acctccaaca | 60 |
| ccagctccaa caatcgccag ccagcctctg tctctgaggc cagaagcttg tagacctgct | 120 |

```
gctggcggag ccgtgcatac aagaggactg gatttcgcct gcgacatcta catctgggcc      180
cctctggctg aacatgtgg cgttctgctg ctgagcctgg tcatcaccct gtactgcaac      240
caccggaac                                                             249
```

<210> SEQ ID NO 16
<211> LENGTH: 336
<212> TYPE: DNA
<213> ORGANISM: Artificial Sequence
<220> FEATURE:
<223> OTHER INFORMATION: Primary signaling domain

<400> SEQUENCE: 16

```
agagtgaagt tcagcaggag cgcagacgcc ccgcgtacc agcagggcca gaaccagctc       60
tataacgagc tcaatctagg acgaagagag gagtacgatg ttttggacaa gagacgtggc     120
cgggaccctg agatggggg aaagccgaga aggaagaacc ctcaggaagg cctgtacaat     180
gaactgcaga aagataagat ggcggaggcc tacagtgaga ttgggatgaa aggcgagcgc     240
cggaggggca aggggcacga tggcctttac cagggtctca gtacagccac caaggacacc     300
tacgacgccc ttcacatgca ggccctgccc cctcgc                               336
```

<210> SEQ ID NO 17
<211> LENGTH: 123
<212> TYPE: DNA
<213> ORGANISM: Artificial Sequence
<220> FEATURE:
<223> OTHER INFORMATION: Co-stimulatory signaling domain

<400> SEQUENCE: 17

```
aggagtaaga ggagcaggct cctgcacagt gactacatga acatgactcc ccgccgcccc      60
gggcccaccc gcaagcatta ccagccctat gccccaccac gcgacttcgc agcctatcgc     120
tcc                                                                   123
```

<210> SEQ ID NO 18
<211> LENGTH: 141
<212> TYPE: DNA
<213> ORGANISM: Artificial Sequence
<220> FEATURE:
<223> OTHER INFORMATION: Co-stimulatory signaling domain

<400> SEQUENCE: 18

```
cgtttctctg ttgttaaacg gggcagaaag aagctcctgt atatattcaa acaaccattt      60
atgagaccag tacaaactac tcaagaggaa gatggctgta gctgccgatt tccagaagaa     120
gaagaaggag gatgtgaact g                                               141
```

<210> SEQ ID NO 19
<211> LENGTH: 51
<212> TYPE: DNA
<213> ORGANISM: Artificial Sequence
<220> FEATURE:
<223> OTHER INFORMATION: Signal peptide

<400> SEQUENCE: 19

```
atgtggctgc agagcctgct gctcttgggc actgtggcct gcagcatctc t               51
```

<210> SEQ ID NO 20
<211> LENGTH: 267
<212> TYPE: DNA
<213> ORGANISM: Artificial Sequence
<220> FEATURE:

<223> OTHER INFORMATION: D1

<400> SEQUENCE: 20

| | |
|---|---|
| agtacaagtg ctggacctac ggttccagac cgtgacaatg atggaatccc tgattcatta | 60 |
| gaggtagaag gatatacggt tgatgtcaaa aataaaagaa cttttctttc accatggatt | 120 |
| tctaatattc atgaaaagaa aggattaacc aaatataaat catctcctga aaaatggagc | 180 |
| acggcttctg atccgtacag tgatttcgaa aaggttacag acggattga taagaatgta | 240 |
| tcaccagagg caagacaccc ccttgtg | 267 |

<210> SEQ ID NO 21
<211> LENGTH: 693
<212> TYPE: DNA
<213> ORGANISM: Artificial Sequence
<220> FEATURE:
<223> OTHER INFORMATION: D2

<400> SEQUENCE: 21

| | |
|---|---|
| gcagcttatc cgattgtaca tgtagatatg gagaatatta ttctctcaaa aaatgaggat | 60 |
| caatccacac agaatactga tagtcaaacg agaacaataa gtaaaaatac ttctacaagt | 120 |
| aggacacata ctagtgaagt acatggaaat gcagaagtgc atgcgtcgtt ctttgatatt | 180 |
| ggtgggagtg tatctgcagg atttagtaat tcgaattcaa gtacggtcgc aattgatcat | 240 |
| tcactatctc tagcagggga aagaacttgg gctgaaacaa tgggtttaaa taccgctgat | 300 |
| acagcaagat taaatgccaa tattagatat gtaaatactg ggacggctcc aatctacaac | 360 |
| gtgttaccaa cgacttcgtt agtgttagga aaaaatcaaa cactcgcgac aattaaagct | 420 |
| aaggaaaacc aattaagtca atacttgca cctaataatt attatccttc taaaaacttg | 480 |
| gcgccaatcg cattaaatgc acaagacgat ttcagttcta ctccaattac aatgaattac | 540 |
| aatcaatttc ttgagttaga aaaaacgaaa caattaagat tagatacgga tcaagtatat | 600 |
| gggaatatag caacatacaa ttttgaaaat ggaagagtga gggtggatac aggctcgaac | 660 |
| tggagtgaag tgttaccgca aattcaagaa aca | 693 |

<210> SEQ ID NO 22
<211> LENGTH: 324
<212> TYPE: DNA
<213> ORGANISM: Artificial Sequence
<220> FEATURE:
<223> OTHER INFORMATION: D3

<400> SEQUENCE: 22

| | |
|---|---|
| actgcacgta tcattttaa tggaaaagat ttaaatctgg tagaaaggcg gatagcggcg | 60 |
| gttaatccta gtgatccatt agaaacgact aaaccggata tgacattaaa agaagccctt | 120 |
| aaaatagcat ttggatttaa cgaaccgaat ggaaacttac aatatcaagg gaaagacata | 180 |
| accgaatttg attttaattt cgatcaacaa acatctcaaa atatcaagaa tcagttagcg | 240 |
| gaattaaacg taactaacat atatactgta ttagataaaa tcaaattaaa tgcaaaaatg | 300 |
| aatattttaa taagagataa acgt | 324 |

<210> SEQ ID NO 23
<211> LENGTH: 420
<212> TYPE: DNA
<213> ORGANISM: Artificial Sequence
<220> FEATURE:
<223> OTHER INFORMATION: D4

<400> SEQUENCE: 23

```
tttcattatg atagaaataa catagcagtt ggggctgatg agtcagtagt taaggaggct      60
catagagaag taattaattc gtcaacagag ggattattgt taaatattga taaggatata     120
agaaaaatat tatcaggtta tattgtagaa attgaagata ctgaagggct taaagaagtt     180
ataaatgaca gatatgatat gttgaatatt tctagtttac ggcaagatgg aaaaacattt     240
atagatttta aaaaatataa tgataaatta ccgttatata taagtaatcc caattataag     300
gtaaatgtat atgctgttac taaagaaaac actattatta atcctagtga gaatggggat     360
actagtacca acgggatcaa gaaaatttta atcttttcta aaaaaggcta tgagatagga     420
```

```
<210> SEQ ID NO 24
<211> LENGTH: 23
<212> TYPE: DNA
<213> ORGANISM: Artificial Sequence
<220> FEATURE:
<223> OTHER INFORMATION: Primer

<400> SEQUENCE: 24
tgctgcacca ctggaatgaa atc                                              23

<210> SEQ ID NO 25
<211> LENGTH: 23
<212> TYPE: DNA
<213> ORGANISM: Artificial Sequence
<220> FEATURE:
<223> OTHER INFORMATION: Primer

<400> SEQUENCE: 25
ctcctcctgg cagaactttc tgg                                              23

<210> SEQ ID NO 26
<211> LENGTH: 28
<212> TYPE: DNA
<213> ORGANISM: Artificial Sequence
<220> FEATURE:
<223> OTHER INFORMATION: Primer

<400> SEQUENCE: 26
ctttcattgt gttttcttct caagcaac                                         28

<210> SEQ ID NO 27
<211> LENGTH: 26
<212> TYPE: DNA
<213> ORGANISM: Artificial Sequence
<220> FEATURE:
<223> OTHER INFORMATION: Primer

<400> SEQUENCE: 27
gttttcaagc ctcctgcttt ctgaat                                           26
```